(12) United States Patent
Coumans et al.

(10) Patent No.: US 12,053,270 B2
(45) Date of Patent: *Aug. 6, 2024

(54) SYSTEMS AND METHODS FOR MAGNETIC RESONANCE IMAGING OF INFANTS

(71) Applicant: Hyperfine Operations, Inc., Guilford, CT (US)

(72) Inventors: Jacobus Coumans, Old Lyme, CT (US); Christopher Thomas McNulty, Guilford, CT (US)

(73) Assignee: Hyperfine Operations, Inc., Guilford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/096,856

(22) Filed: Jan. 13, 2023

(65) Prior Publication Data

US 2023/0346242 A1 Nov. 2, 2023

Related U.S. Application Data

(63) Continuation of application No. 16/815,534, filed on Mar. 11, 2020, now Pat. No. 11,553,853.

(Continued)

(51) Int. Cl.
*A61B 5/055* (2006.01)
*A61B 5/242* (2021.01)
(Continued)

(52) U.S. Cl.
CPC .............. *A61B 5/055* (2013.01); *A61B 5/242* (2021.01); *G01R 33/287* (2013.01);
(Continued)

(58) Field of Classification Search
CPC ... A61B 5/055; A61B 5/242; A61B 2503/045; A61B 2560/0431; A61B 2503/04;
(Continued)

(56) References Cited

U.S. PATENT DOCUMENTS 4,774,468 A 9/1988 Bydder
5,490,508 A 2/1996 Kato
(Continued)

FOREIGN PATENT DOCUMENTS

CN 202196164 U 4/2012
CN 105358053 A 2/2016
(Continued)

OTHER PUBLICATIONS

International Search Report and Written Opinion for International Application No. PCT/US2020/021969 mailed May 15, 2020.
(Continued)

*Primary Examiner* — G.M. A Hyder
(74) *Attorney, Agent, or Firm* — Foley & Lardner LLP

(57) ABSTRACT

According to some aspects, a system configured to facilitate imaging an infant using a magnetic resonance imaging (MRI) device is provided herein. The system comprises an infant-carrying apparatus comprising an infant support configured to support the infant and an isolette for positioning the infant relative to the MRI device, the isolette comprising: a base for supporting the infant-carrying apparatus; and a bottom surface configured to be coupled to the MRI device. In some embodiments, the infant-carrying apparatus further comprises at least one radio frequency (RF) coil coupled to the infant support and configured to be coupled to the MRI device to detect MR signals during imaging performed by the MRI device. A method for positioning an infant relative to an MRI device using an infant-carrying apparatus and isolette is further provided herein.

20 Claims, 15 Drawing Sheets

Related U.S. Application Data

(60) Provisional application No. 62/817,455, filed on Mar. 12, 2019.

(51) Int. Cl.
    *G01R 33/28*       (2006.01)
    *G01R 33/385*    (2006.01)
    *G01R 33/44*     (2006.01)
    *G01R 33/54*     (2006.01)

(52) U.S. Cl.
    CPC ......... *G01R 33/385* (2013.01); *G01R 33/445* (2013.01); *G01R 33/54* (2013.01); *A61B 2503/045* (2013.01); *A61B 2560/0431* (2013.01)

(58) Field of Classification Search
    CPC ...... A61B 5/0046; A61B 5/70; G01R 33/287; G01R 33/385; G01R 33/445; G01R 33/54; G01R 33/3802; A61G 11/006; A61G 11/007; A61G 2210/50; A61G 11/00
See application file for complete search history.

(56) References Cited

U.S. PATENT DOCUMENTS

| | | | |
|---|---|---|---|
| 7,315,168 | B2 | 1/2008 | Rapoport et al. |
| 7,400,147 | B2 | 7/2008 | Rapoport |
| 9,541,616 | B2 | 1/2017 | Rothberg et al. |
| 9,547,057 | B2 | 1/2017 | Rearick et al. |
| 9,625,544 | B2 | 4/2017 | Poole et al. |
| 9,645,210 | B2 | 5/2017 | McNulty et al. |
| 9,817,093 | B2 | 11/2017 | Rothberg et al. |
| 10,145,913 | B2 | 12/2018 | Hugon et al. |
| 10,145,922 | B2 | 12/2018 | Rothberg et al. |
| 10,222,434 | B2 | 3/2019 | Poole et al. |
| 10,274,561 | B2 | 4/2019 | Poole et al. |
| 10,281,540 | B2 | 5/2019 | Mileski et al. |
| 10,281,541 | B2 | 5/2019 | Poole et al. |
| 10,310,037 | B2 | 6/2019 | McNulty et al. |
| 10,416,264 | B2 | 9/2019 | Sofka et al. |
| 10,551,452 | B2 | 2/2020 | Rearick et al. |
| 10,591,561 | B2 | 3/2020 | Sacolick et al. |
| 10,709,387 | B2 | 7/2020 | Poole et al. |
| 11,553,853 | B2 * | 1/2023 | Coumans ............. G01R 33/385 |
| 2002/0173717 | A1 | 11/2002 | Rohling et al. |
| 2004/0015074 | A1 | 1/2004 | Srinivasan |
| 2004/0075437 | A1 | 4/2004 | Srinivasan |
| 2005/0113668 | A1 | 5/2005 | Srinivasan |
| 2008/0231278 | A1 | 9/2008 | Ishihara et al. |
| 2009/0179643 | A1 | 7/2009 | Lin |
| 2012/0126814 | A1 | 5/2012 | Fischer et al. |
| 2014/0159727 | A1 | 6/2014 | Lee et al. |
| 2016/0069975 | A1 | 3/2016 | Rothberg et al. |
| 2016/0089055 | A1 | 3/2016 | Rapoport |
| 2016/0128592 | A1 | 5/2016 | Rosen et al. |
| 2016/0131727 | A1 | 5/2016 | Sacolick et al. |
| 2016/0334479 | A1 | 11/2016 | Poole et al. |
| 2017/0212192 | A1 | 7/2017 | Rapoport et al. |
| 2018/0070852 | A1 | 3/2018 | Azulay et al. |
| 2018/0153435 | A1 | 6/2018 | Rapoport et al. |
| 2018/0168527 | A1 | 6/2018 | Poole et al. |
| 2019/0038233 | A1 | 2/2019 | Poole et al. |
| 2019/0324098 | A1 | 10/2019 | McNulty et al. |
| 2019/0328271 | A1 | 10/2019 | Rabinovitz |
| 2019/0328596 | A1 | 10/2019 | Rapoport et al. |
| 2019/0353723 | A1 | 11/2019 | Dyvorne et al. |
| 2019/0353726 | A1 | 11/2019 | Poole et al. |
| 2020/0022611 | A1 | 1/2020 | Nelson et al. |
| 2020/0022612 | A1 | 1/2020 | McNulty et al. |
| 2020/0034998 | A1 | 1/2020 | Schlemper et al. |
| 2020/0041588 | A1 | 2/2020 | O'Halloran et al. |
| 2020/0045112 | A1 | 2/2020 | Sacolick et al. |
| 2020/0058106 | A1 | 2/2020 | Lazarus et al. |
| 2020/0150202 | A1 | 5/2020 | Hugon et al. |
| 2020/0200844 | A1 | 6/2020 | Boskamp et al. |
| 2020/0209334 | A1 | 7/2020 | O'Halloran et al. |
| 2020/0289019 | A1 | 9/2020 | Schlemper et al. |
| 2020/0289022 | A1 | 9/2020 | Coumans et al. |
| 2020/0294229 | A1 | 9/2020 | Schlemper et al. |
| 2020/0294282 | A1 | 9/2020 | Schlemper et al. |
| 2020/0294287 | A1 | 9/2020 | Schlemper et al. |
| 2020/0337587 | A1 | 10/2020 | Sacolick et al. |
| 2020/0352473 | A1 | 11/2020 | Chen et al. |
| 2020/0355765 | A1 | 11/2020 | Chen et al. |
| 2021/0048498 | A1 | 2/2021 | Dyvorne et al. |
| 2021/0121066 | A1 | 4/2021 | Rheineck et al. |

FOREIGN PATENT DOCUMENTS

| | | | |
|---|---|---|---|
| CN | 109069057 | A | 12/2018 |
| CN | 208464520 | U | 2/2019 |
| JP | S64-86961 | A | 3/1989 |
| WO | WO-2013/115846 | A1 | 8/2013 |
| WO | WO 2017/183024 | A1 | 10/2017 |

OTHER PUBLICATIONS

Invitation to Pay Additional Fees for International Application No. PCT/US2020/030935 mailed Aug. 24, 2020.
International Search Report and Written Opinion for International Application No. PCT/US2020/030935 mailed Oct. 15, 2020.
International Preliminary Report on Patentability for International Application No. PCT/US2020/021969 mailed Sep. 23, 2021.
International Preliminary Report on Patentability for International Application No. PCT/US2020/030935 mailed Nov. 18, 2021.
U.S. Appl. No. 16/815,534, filed Mar. 11, 2020, Coumans et al.
U.S. Appl. No. 16/864,848, filed May 1, 2020, Chen et al.
U.S. Appl. No. 16/864,859, filed May 1, 2020, Chen et al.
PCT/US2020/021969, May 15, 2020, International Search Report snd Written Opinion.
PCT/US2020/030935, Aug. 24, 2020, Invitation to Pay Additional Fees.
PCT/US2020/030935, Oct. 15, 2020, International Search Report and Written Opinion.
PCT/US2020/021969, Sep. 23, 2021, International Prelimiary Report on Patentability.
PCT/US2020/030935, Nov. 18, 2021, International Preliminary Report on Patentability.
Communication pursuant to Article 94(3) EPC for EP App. No. 20717037.4 dated Jan. 4, 2024.
First Office Action and Search Report for CN App. No. 202080035026.3 dated Dec. 7, 2023 (with partial English translation, 21 pages).
First Office Action for CN App. No. 202080049206.7 dated Mar. 1, 2024 (with English translation, 37 pages).

\* cited by examiner

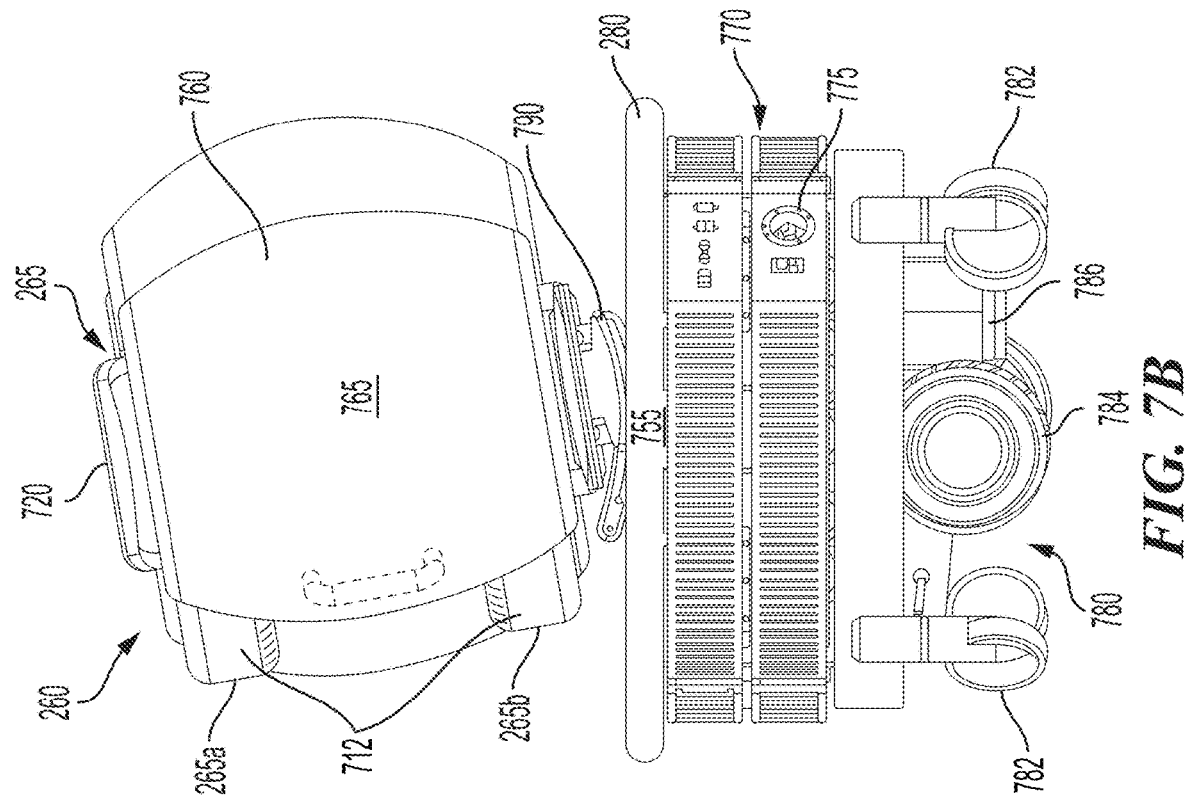
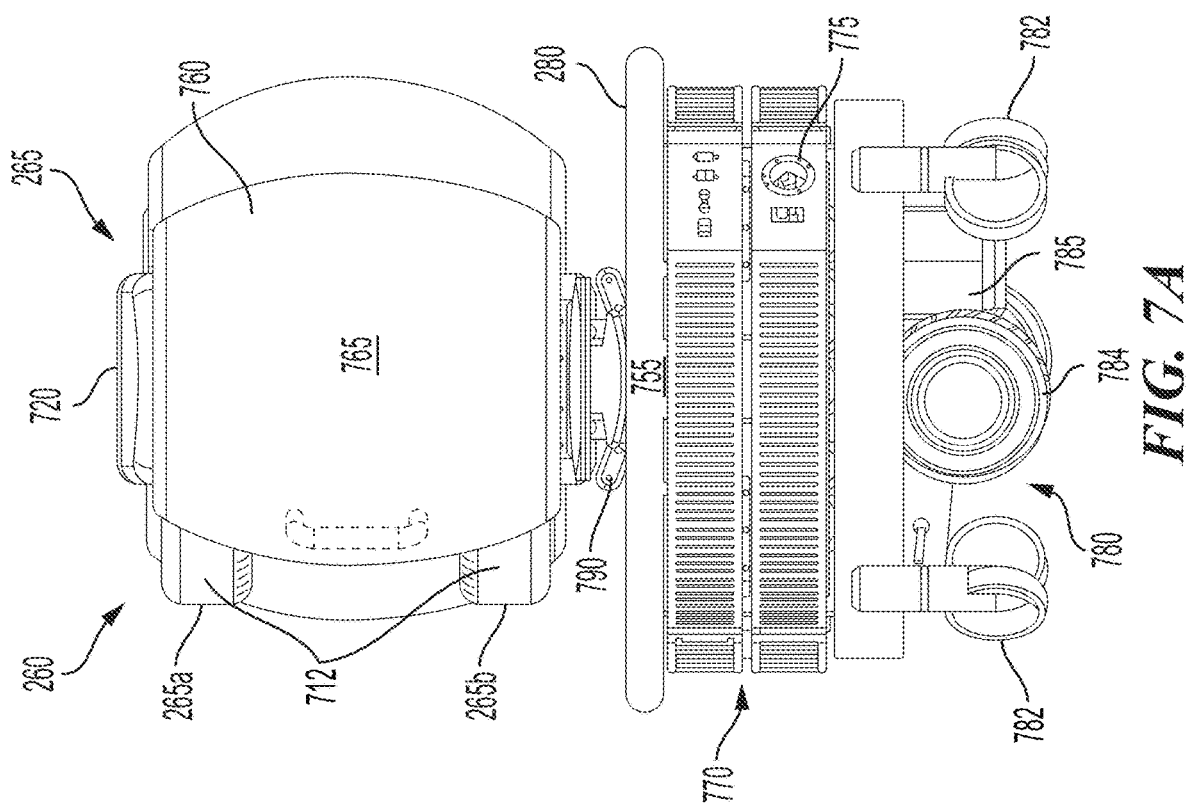
FIG. 7A
FIG. 7B

SYSTEMS AND METHODS FOR MAGNETIC RESONANCE IMAGING OF INFANTS

CROSS-REFERENCE TO RELATED APPLICATIONS

This application is a continuation of and claims priority under 35 U.S.C. § 120 to U.S. application Ser. No. 16/815,534, titled "SYSTEMS AND METHODS FOR MAGNETIC RESONANCE IMAGING OF INFANTS", filed Mar. 11, 2020, which claims the benefit under 35 U.S.C. § 119(e) of U.S. provisional patent application Ser. No. 62/817,455, entitled "MAGNETIC RESONANCE ISOLETTE METHODS AND APPARATUS", filed Mar. 12, 2019, each of which is incorporated by reference in its entirety herein.

FIELD

The present disclosure relates generally to magnetic resonance imaging (MRI) and, more specifically, to systems and methods for positioning an infant patient at least partially within an MRI device to facilitate imaging of the infant using the MRI device.

BACKGROUND

Magnetic resonance imaging provides an important imaging modality for numerous applications and is widely utilized in clinical and research settings to produce images of the inside of the human body. MRI is based on detecting magnetic resonance (MR) signals, which are electromagnetic waves emitted by atoms in response to state changes resulting from applied electromagnetic fields. For example, nuclear magnetic resonance (NMR) techniques involve detecting MR signals emitted from the nuclei of excited atoms upon the re-alignment or relaxation of the nuclear spin of atoms in an object being imaged (e.g., atoms in the tissue of the human body). Detected MR signals may be processed to produce images, which in the context of medical applications, allows for the investigation of internal structures and/or biological processes within the body for diagnostic, therapeutic and/or research purposes.

MRI provides an attractive imaging modality for biological imaging due to the ability to produce non-invasive images having relatively high resolution and contrast without the safety concerns of other modalities (e.g., without needing to expose the subject to ionizing radiation, e.g., x-rays, or introducing radioactive material to the body). Additionally, MRI is particularly well suited to provide soft tissue contrast, which can be exploited to image subject matter that other imaging modalities are incapable of satisfactorily imaging. Moreover, MR techniques are capable of capturing information about structures and/or biological processes that other modalities are incapable of acquiring. However, there are a number of drawbacks to MRI that, for a given imaging application, may involve the relatively high cost of the equipment, limited availability and/or difficulty in gaining access to clinical MRI scanners and/or the length of the image acquisition process.

SUMMARY

Some embodiments provide for a system configured to facilitate imaging an infant using a magnetic resonance imaging (MRI) device, the system comprising: an infant-carrying apparatus comprising an infant support configured to support the infant; and an isolette for positioning the infant relative to the MRI device, the isolette comprising: a base for supporting the infant-carrying apparatus; and a bottom surface configured to be coupled to the MRI device.

In some embodiments, the infant-carrying apparatus further comprises at least one radio frequency (RF) coil coupled to the infant support and configured to be coupled to the MRI device to detect MR signals during imaging performed by the MRI device. In some embodiments, the at least one RF coil is integrated with the infant support. In some embodiments the at least one RF coil comprises an RF head coil coupled to the infant support at a position for at least partially encircling the infant's head. In some embodiments, the at least one RF coil comprises a RF body coil coupled to the infant support at a first position for at least partially encircling the infant's body, and an RF head coil coupled to the infant support at a second position for at least partially encircling the infant's head. In some embodiments, the at least one RF coil is further configured to transmit RF pulses according to one or more pulse sequences during imaging performed by the MRI device.

In some embodiments, the infant support comprises a jacket and padding coupled to the jacket. In some embodiments, the jacket comprises a right side and a left side, the left side and the right side being configured to be coupled together via at least one fastener.

In some embodiments, the isolette has a height of 40 centimeters or less. In some embodiments, the isolette has a width of 150 centimeters or less. In some embodiments, the bottom surface of the isolette comprises a recessed portion shaped to receive a complementary portion of the MRI device. In some embodiments, the recessed portion comprises at least one track, the at least one track being configured to receive a complementary portion of the MRI device. In some embodiments, the system further comprises a padding disposed on the base, wherein the padding comprises first and second raised portions and the infant-carrying apparatus is configured to be received between the first and second raised portions of the padding.

In some embodiments, the system further comprises the MRI device, the MRI device comprising a magnetics system having a plurality of magnetics components configured to produce magnetic fields for performing magnetic resonance imaging, the magnetics system comprising a permanent $B_0$ magnet configured to produce a $B_0$ field for magnetic resonance imaging, and a plurality of gradient coils. In some embodiments, the system further comprises a bridge coupled to the MRI device and configured to support at least a portion of the isolette. In some embodiments, the bridge is removably mounted to the MRI device. In some embodiments, the $B_0$ magnet comprises: at least one first permanent $B_0$ magnet to produce a magnetic field to contribute to the $B_0$ field for the MRI device, and at least one second permanent $B_0$ magnet to produce a magnetic field to contribute to the $B_0$ field for the MRI device, wherein the at least one first $B_0$ magnet and the at least one second $B_0$ magnet are arranged relative to one another so that an imaging region is provided therebetween, wherein the isolette is at least partially disposed within the imaging region when the isolette is coupled to the MRI device.

Some embodiments provide for a method for positioning an infant relative to a magnetic resonance imaging (MRI) device, the method comprising: positioning the infant in an infant-carrying apparatus, the infant-carrying apparatus comprising: an infant support configured to support the infant; and at least one radio frequency (RF) coil coupled to the infant support and configured to be coupled to the MRI device to detect MR signals during imaging performed by the MRI device; wrapping the infant support at least partially around the infant; placing the infant support and infant in an isolette configured to be coupled to the MRI device; and removably coupling the isolette to the MRI device to position at least a part of the infant in an imaging region of the MRI device.

In some embodiments, the method further comprises, after positioning at least the part of the infant in the imaging region of the MRI device, using the MRI device and the at least one RF coil to obtain at least one magnetic resonance image of at least the part of the infant. In some embodiments, the method further comprises, after obtaining the at least one magnetic resonance image, removing the infant from the imaging region of the MRI device by decoupling the isolette from the MRI device. In some embodiments, the method further comprises, after decoupling the isolette from the MRI device, removing the infant and the infant-carrying apparatus from the isolette. In some embodiments, the method further comprises obtaining at least one first magnetic resonance image of at least the part of the infant. In some embodiments, the infant support comprises a right side and a left side, and wrapping the infant support at least partially around the infant comprises coupling the left side of the infant support to the right side of the infant support via at least one fastener. In some embodiments, placing the infant support and the infant in the isolette comprises placing the infant support and infant between first and second raised portions of a padding of the isolette. In some embodiments, the method further comprises positioning the infant on the infant support so that the infant's head is at least partially encircled by the at least one RF coil. In some embodiments, the method further comprises positioning the infant on the infant support so that the infant's body is at least partially encircled by the at least one RF coil. In some embodiments, the method further comprises coupling the at least one RF coil to the MRI device.

Some embodiments provide for an infant-carrying apparatus to facilitate imaging an infant using a magnetic resonance imaging (MRI) device, the apparatus comprising: an infant support to support the infant during imaging, the infant support comprising: a jacket; and padding coupled to the jacket; and at least one radio frequency (RF) coil integrated with the infant support, the at least one RF coil configured to detect MR signals during MR imaging.

In some embodiments, the at least one RF coil comprises a RF head coil coupled to the infant support at a position for at least partially encircling the infant's head. In some embodiments, the at least one RF coil comprises a RF body coil coupled to the infant support at a position for at least partially encircling the infant's body. In some embodiments, the at least one RF coil comprises a RF body coil coupled to the infant support at a first position for at least partially encircling the infant's body, and a RF head coil coupled to the infant support at a second position for at least partially encircling the infant's head. In some embodiments, the RF body coil is further configured to transmit RF pulses according to one or more pulse sequences during imaging performed by the MRI device.

In some embodiments, the jacket comprises a left side and a right side, and the left side of the jacket is configured to be coupled to the right side of the jacket via at least one fastener.

In some embodiments, the infant-carrying apparatus comprises a portion of a magnetic resonance imaging system comprising the MRI device, the MRI device comprising a magnetics system having a plurality of magnetics components configured to produce magnetic fields for performing magnetic resonance imaging, the magnetics system comprising a permanent $B_0$ magnet configured to produce a $B_0$ field for the magnetic resonance imaging system; and a plurality of gradient coils. In some embodiments, the MRI device further comprises at least one second RF coil configured to transmit RF pulses according to one or more pulse sequences during imaging, the at least one second RF coil being different from the at least one RF coil integrated with the infant support.

Some embodiments include an isolette for positioning an infant relative to a magnetic resonance imaging (MRI) device, the isolette comprising: a base for supporting the infant; and a bottom surface configured to be coupled to the MRI device.

In some embodiments, the isolette has a height of 40 centimeters or less. In some embodiments, the isolette has a width of 150 centimeters or less.

In some embodiments, the bottom surface comprises a recessed portion being shaped to receive a complementary portion of the MRI device. In some embodiments, the recessed portion comprises at least one track, the at least one track being configured to receive a wing of the complementary portion of the MRI device.

In some embodiments, the isolette further comprises an enclosure configured for receiving the infant therein, the enclosure comprising one or more walls extending upward from the base, wherein at least one of the one or more walls is removably coupled to the base. In some embodiments, the isolette further comprises an enclosure configured for receiving the infant therein, the enclosure comprising one or more walls extending upward from the base, wherein at least one of the one or more walls is configured to be folded. In some embodiments, the at least one of the one or more walls is configured to be folded along a hinge coupled to the base. In some embodiments, the at least one of the one or more walls is configured to be folded along a hinge coupled to another of the one or more walls.

In some embodiments, the isolette further comprises a padding disposed on the base, wherein the padding comprises first and second raised portions, and the infant is configured to be received between the first and second raised portions of the padding.

In some embodiments, the isolette further comprises an enclosure configured for receiving the infant therein, the enclosure comprising one or more walls extending upward from the base; at least one inlet coupled to the base and configured to be coupled to a source of air; and one or more vents disposed in the enclosure and coupled to at least one inlet, such that air from the source of air is provided to the enclosure via the one or more vents. In some embodiments, a temperature inside the enclosure is controlled at least in part by controlling the air provided to the enclosure.

BRIEF DESCRIPTION OF THE DRAWINGS

Various aspects and embodiments of the disclosed technology will be described with reference to the following figures. It should be appreciated that the figures are not necessarily drawn to scale. For purposes of clarity, not every component may be labeled in every drawing.

FIGS. 7A-7B illustrate an example MRI device, in accordance with some embodiments of the technology described herein.

DETAILED DESCRIPTION

Figure 1:
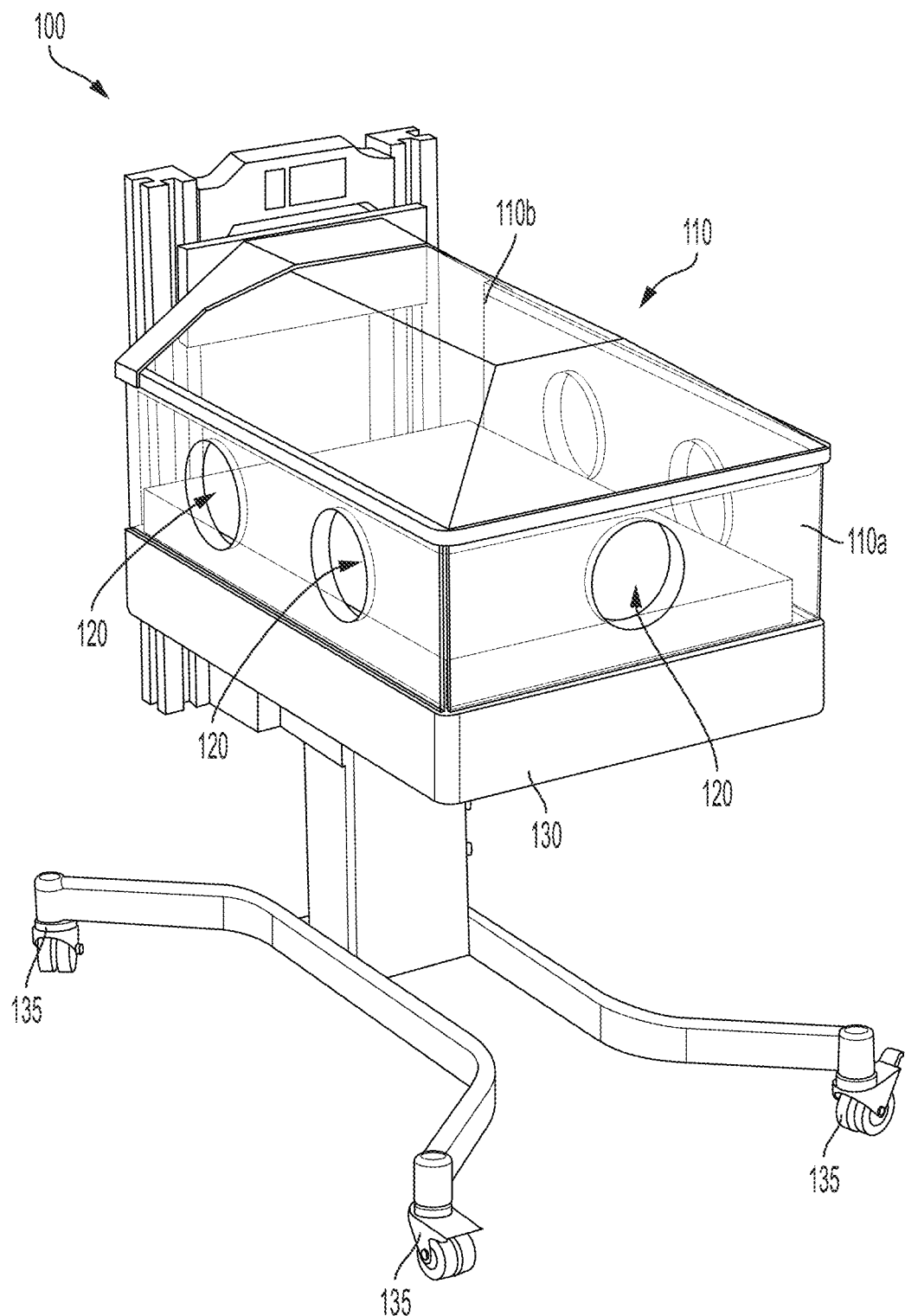
FIG. 1 illustrates a conventional infant isolette.

The inventors have recognized that infant and, in particular, neonatal care is an area in which the benefits of MRI are often unavailable due to the drawbacks of conventional MRI devices. There are on the order of 1,000 Neonatal Intensive Care Units (NICUs) in the United States alone. The average number of beds (or NICU stations) is 21 per NICU for a total of 21,000 beds. Neonates (infants within the first 28 days after birth) are often kept in "isolettes," which are specialized incubators or enclosed cribs that typically allow for controlled environment (e.g., by controlling temperature, humidity and/or oxygen levels) in which the infant is protected from outside contaminants. An isolette is usually constructed using clear plastic material and often includes armholes through which the infant can be reached without significantly disturbing the controlled environment of the isolette. The isolette is also typically constructed to facilitate continuous monitoring of the infant's biological signals (e.g., temperature, heart rate, oxygen saturation, etc.).

The inventors have appreciated that despite providing a potent diagnostic modality for investigating infant (e.g., neonate) complications (e.g., abnormal infant brain function), MRI is often unavailable to infants in need of this technology. Conventional MRI devices are predominantly high-field systems requiring dedicated facilities (e.g., virtually all deployed MRI devices in the U.S. operate at 1.5 T (Tesla) or 3.0 T field strengths, with higher field strengths of 7 T and 9 T used in research settings). As a result, a hospital's MRI installment is typically located in the radiology department. Transporting an infant from the controlled environment of its isolette to the MRI device and positioning the infant within the MRI device is a complicated, personnel intensive and risky process. For infants, the trip between the NICU and the radiology department actually can be life threatening, and it requires a team of hospital personnel from various backgrounds (nurses, respiratory experts, physicians) to guide the trip.

Some attempts have been made to make the trip between the NICU department and the radiology department easier. In particular, special incubators have been designed to hold an infant during the trip to make transportation safer. However, these specialized incubators do not avoid having to carefully handle the infant multiple times, as the infant must be moved from the NICU isolette into the specialized incubator, transported to the MRI device, positioned within the MRI device and the reverse of this process performed to return the infant to the NICU isolette. This complicated and potentially dangerous process must be repeated each time the infant is to undergo an MRI, virtually eliminating the possibility of repeat MRI scans.

Moreover, although attempts have been made to co-locate high-field MRI devices physically within the NICU, the size, weight, and cost of these systems make this approach impractical. Even if such a system were located in a NICU, the problem of transporting the infant from the isolette to the MRI device persists. Specifically, the infant must still be removed from the isolette and positioned onto a table top that will enter into the cylindrical bore of the MRI device. The process of doing so can be complicated due to the many physiological sensors coupled to the infant which must be gathered and reconnected when the infant is positioned within the MRI device. The time spent outside of the isolette and within the bore of the MRI device can also be life-threatening for an infant who cannot maintain its body heat and requires a controlled environment to be protected from drafts and cold.

Thus, the inventors have developed an MR isolette system configured to facilitate imaging an infant using an MRI device. In some embodiments, the MR isolette system comprises: (1) an infant-carrying apparatus configured to facilitate transporting an infant between a conventional isolette and the MRI device for imaging; and (2) an MR isolette configured to be coupled to the MRI device and for supporting the infant-carrying apparatus. The MR isolette allows for the infant to remain in a controlled environment during imaging.

In some embodiments, the infant-carrying apparatus may include an infant support having a jacket and padding coupled to the jacket for wrapping around and supporting the infant during transport and imaging. The infant-carrying apparatus may further include at least one radio frequency (RF) coil coupled to (e.g., integrated with) the jacket and configured to detect MR signals during MR imaging, which allows for improved detection of MR signals due to the coil's proximity to the infant.

In some embodiments, the MR isolette comprises a base for supporting the infant and infant-carrying apparatus and a bottom surface configured to be coupled to the MR device. The MR isolette may be dimensioned such that the MR isolette can be inserted into the imaging region of an MRI device while providing a controlled environment for the infant during imaging.

The inventors have also developed a method for positioning an infant relative to the MRI device using the MR isolette system. In some embodiments, the method may include positioning the infant in the infant-carrying apparatus by wrapping the infant support at least partially around the infant, placing the infant support and infant into the MR isolette (e.g., by using the infant-carrying apparatus to move the infant from a conventional NICU isolette to the MR isolette), and positioning at least a part of the infant in an imaging region of the MRI device by removably coupling the isolette to the MRI device.

The MR isolette system developed by the inventors may be used with POC MRI devices such as the devices and systems described in U.S. Pat. No. 10,222,434 ('434), titled "Portable Magnetic Resonance Imaging Methods and Apparatus," filed Jan. 24, 2019 under, which is hereby incorporated by reference in its entirety. Specifically, in some embodiments, the MR isolette system may be configured to be positioned at least partially within the imaging region of a POC MRI device and to be coupled (e.g., mechanically and/or electrically) to the POC MRI device. For example, the MR isolette system may be coupled mechanically to the POC MRI device (e.g., by inserting a complementary portion of the MRI device into a receptacle formed in a base of the MR isolette, as shown in FIG. 3B). Securing the MR isolette to the MRI device facilitates precise positioning of the infant in the imaging region of the MRI device and prevents inadvertent movement during imaging increasing the quality of acquired MR images. The MR isolette system may be also coupled electrically to the POC MRI device. For example, the infant-carrying apparatus of the MR isolette system may include at least one RF coil which may be electrically coupled (e.g., via a connector) to the POC MRI device so that it can be used as a receive and/or transmit RF coil during imaging performed on the infant by the POC MRI device.

The MR isolette system described herein may be used with any suitable open MRI device, as aspects of the technology described herein are not limited in this respect. Although the MR isolette system is described herein as being coupled to a POC MRI device, for example the POC MRI devices described with reference to FIGS. 6-8 herein and in the '434 patent, in some embodiments, the MR isolette system may be coupled to other types of open MRI devices.

As used herein, "high-field" refers generally to MRI devices presently in use in a clinical setting and, more particularly, to MRI devices operating with a main magnetic field (i.e., a $B_0$ field) at or above 1.5 T, though clinical systems operating between 0.5 T and 1.5 T are often also characterized as "high-field." Field strengths between approximately 0.2 T and 0.5 T have been characterized as "mid-field" and, as field strengths in the high-field regime have continued to increase, field strengths in the range between 0.5 T and 1 T have also been characterized as mid-field. By contrast, "low-field" refers generally to MRI devices operating with a $B_0$ field of less than or equal to approximately 0.2 T, though systems having a $B_0$ field of between 0.2 T and approximately 0.3 T have sometimes been characterized as low-field as a consequence of increased field strengths at the high end of the high-field regime. Within the low-field regime, low-field MRI devices operating with a $B_0$ field of less than 0.1 T are referred to herein as "very low-field" and low-field MRI devices operating with a $B_0$ field of less than 10 mT are referred to herein as "ultra-low field."

The aspects and embodiments described above, as well as additional aspects and embodiments, are described further below. These aspects and/or embodiments may be used individually, all together, or in any combination, as the technology is not limited in this respect.

FIG. 1 illustrates a conventional infant isolette 100 configured to provide a controlled protective environment for neonates and other infants. Isolette 100 includes a clear plastic bassinet 110 having walls 110a and cover 110b. Armholes 120 are provided through walls 110a to allow access to the infant. Bassinet 110 is supported by a frame 130 having wheels 135 that allow the isolette to be moved to desired locations. Isolette 100 includes air vents (not shown) that allow the temperature and humidity of the bassinet's interior to be controlled.

As discussed above, performing MRI on an infant typically requires a team of specialists to transport the infant to the radiology department and back, a process involving multiple transitions for, and handling of the infant, including the imaging process itself. Even in the rare case where the NICU has a specialized neonate MRI scanner, the infant still must be removed from the isolette and placed on a specialized table that draws the infant into the bore of the MRI device. Any time spent outside of an isolette provides risks for the infant. Additionally, the infant disappears from sight when inserted into the cylindrical bore of the system, which can be quite alarming for the infant's parents. As such, in some instances, the infant may need to be moved back and forth between the isolette and the MRI device during successive rounds of imaging, thus increasing the risk of transport and length of the imaging process. After the imaging procedure is completed, the infant must then be returned to the isolette. This process must be repeated each time MRI is to be performed.

Figure 6:
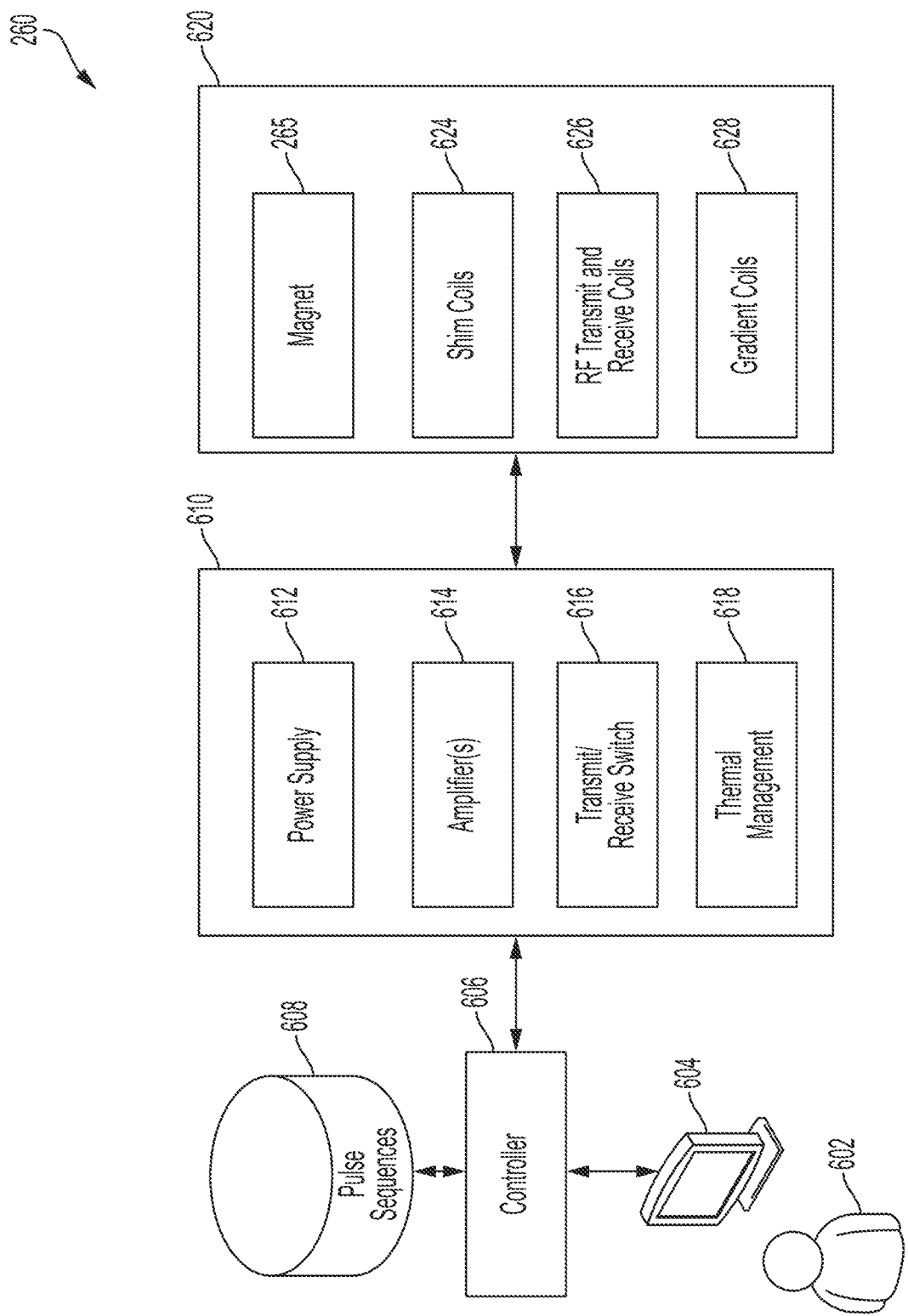
FIG. 6 illustrates example components of a magnetic resonance imaging device, in accordance with some embodiments of the technology described herein.
Figure 8:
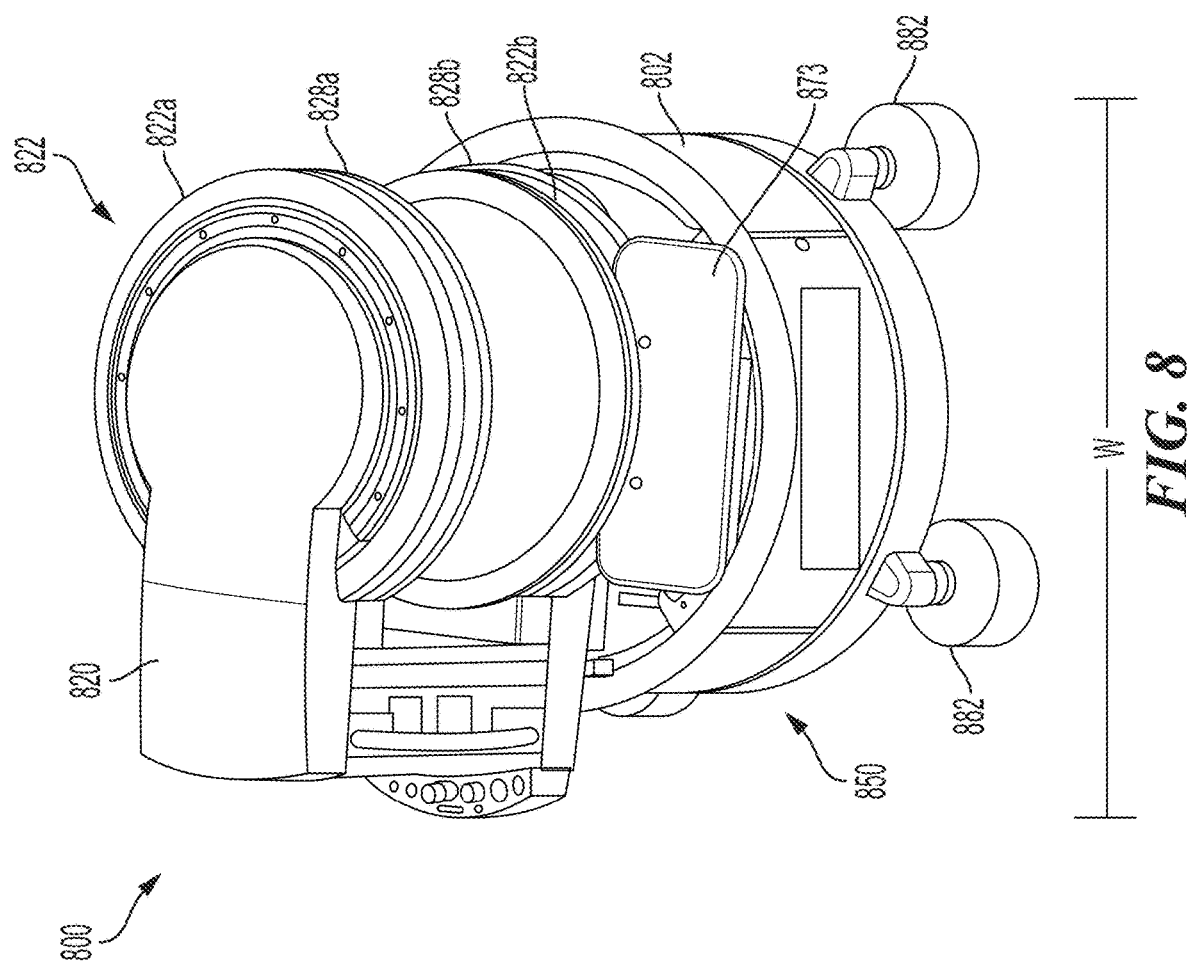
FIG. 8 illustrates another example MRI device, in accordance with some embodiments of the technology described herein.

The MR isolette system developed by the inventors and described herein allows for a simple transition between a conventional isolette (e.g., the isolette shown in FIG. 1) and a POC MRI device (e.g., as described herein including with reference to FIGS. 6-8 and examples of which are provided in the '434 patent, which is incorporated by reference herein in its entirety). For example, the MR isolette system described herein requires only a single movement of the infant: from the conventional isolette to the MR isolette. The transition to the MR isolette is facilitated by the infant-carrying apparatus of the MR isolette system which secures the infant during the transition from the conventional isolette to the MR isolette and provides for orderly transport of electrical wires which may be coupled to the infant. Once in the MR isolette, the infant can be positioned at least partially within an imaging region of the MRI device for MR imaging, without disappearing from sight. In particular, the bi-planar arrangement of $B_0$ magnets of the MRI device provides for an imaging region having an open nature sufficient to keep the infant visible during imaging through transparent walls of the MR isolette. The open nature of the imaging region of the MRI device further accommodates various other devices (e.g., one or more electrical leads coupled to the infant) to stay connected to the infant during imaging, and the low-field nature of the MRI device (in some embodiments) prevents the $B_0$ field from interfering with such devices.

Thus, according to some embodiments of the technology described herein, the inventors have developed a MR isolette system comprising a MR isolette and an infant-carrying apparatus. The MR isolette integrates a "gap" isolette which may be configured to couple to a Point of Care MRI device to provide a standalone MR isolette solution. The gap isolette, also referred to herein as an "MR isolette," may comprise an enclosed crib being adapted for use with an MRI device, as described herein. The MR isolette facilitates MR scanning of an infant, such as a neonate, at will, without requiring frequent transport of the infant to and from the MRI device outside of an isolette. Thus, the MR isolette described herein may eliminate or reduce the risks associated with transporting an infant from a conventional isolette to an MRI device, as the steps required for moving an infant from the conventional isolette to an MR isolette involve little or no risk to the infant.

Figure 2:
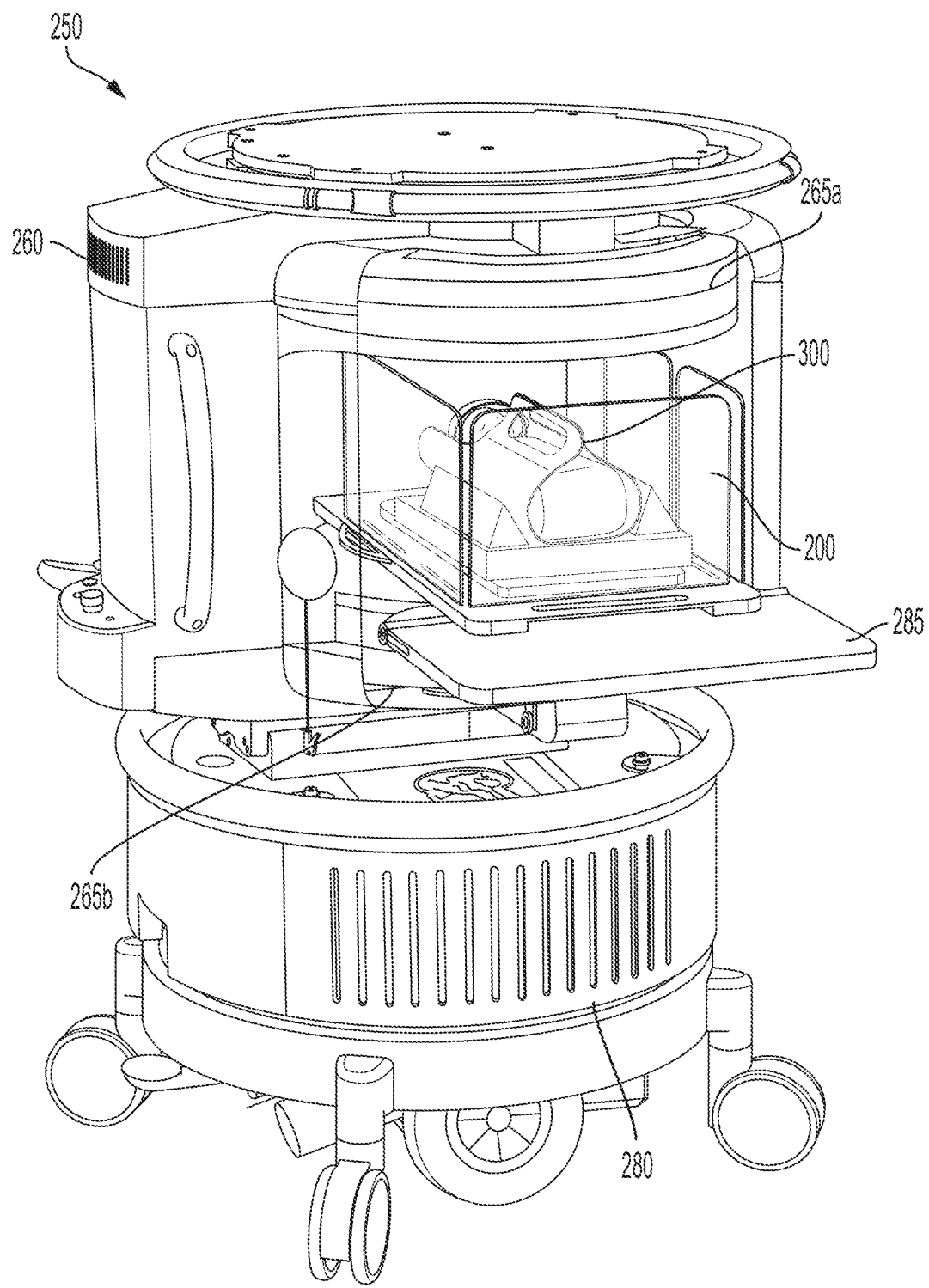
FIG. 2 illustrates an example MR isolette system coupled to an MRI device, in accordance with some embodiments of the technology described herein.

As one example, FIG. 2 illustrates an MR isolette system 250 coupled to an MRI device 260, in accordance with some embodiments. Example MR isolette system 250 comprises MR isolette 200 which provides a controlled environment for an infant during MR imaging and infant-carrying apparatus 300 which may be positioned around the infant to facilitate safe transport of the infant to the MR isolette 200, for example from the conventional isolette shown in FIG. 1 or other location. Infant-carrying apparatus 300 further provides for secure positioning of the infant in the MR isolette 200 during imaging. Aspects of MR isolette 200 and infant-carrying apparatus 3000 are described in further detail below.

As described herein, the MR isolette system 250 may be coupled to an MRI device, for example, MRI device 260 shown in FIG. 2. MRI device 260 may be, for example, similar or the same as any of the example low-field MRI devices described in the '434 patent incorporated by reference herein. In the illustrated embodiment, MRI device 260 has an open configuration formed by a pair of $B_0$ magnets 265a, 265b provided in a bi-planar arrangement to form an imaging region between upper $B_0$ magnet 265a and lower $B_0$ magnet 265b. MRI device 260 further comprises a base 280 to support the $B_0$ magnets 265a, 265b. MR isolette 200 is configured to maintain a controlled environment for the infant like a conventional isolette, but is dimensioned to allow the MR isolette 200 to be positioned at least partially within the imaging region of MRI device 260 between upper and lower $B_0$ magnets 265a, 265b, and includes features that allow the MR isolette 260 to be utilized within the MRI device 260, as described in further detail below. As shown in FIG. 2, MR isolette 200 may be positioned on a bridge 285 of the MRI device 260, and the MR isolette 200 can be moved along bridge 285 at least partially into an imaging region of the MRI device 260.

As described herein, MR isolette 200 may be configured having sufficiently small dimensions such that the MR isolette 200 can be at least partially inserted into an imaging region of the MRI device 260 between the upper and lower $B_0$ magnets 265a, 265b. For example, in some embodiments, the MR isolette has a height less than or equal to 50 cm, less than or equal to 45 cm, less than or equal to 40 cm, less than or equal to 35 cm, less than or equal to 30 cm, or any height within the ranges listed herein or any other suitable height such that the MR isolette can be inserted at least partially into an imaging region of the MRI device between upper and lower $B_0$ magnets. In some embodiments, the MR isolette has a width less than or equal to 150 cm, less than or equal to 140 cm, less than or equal to 130 cm, less than or equal to 125 cm, less than or equal to 120 cm, or any width within the ranges listed herein or any other suitable width such that the MR isolette can be inserted at least partially into an imaging region of the MRI device between upper and lower $B_0$ magnets.

Because MR isolette 200 can be positioned within the MRI device 260, there is no need to return the infant to the conventional isolette after an image acquisition is performed. Specifically, the infant is safely positioned within a controlled environment while in the MR isolette 200, so there is no need to rush the infant to a separate isolette between image acquisitions, instead allowing the infant to remain in the imaging region of the MRI device 260 for as long as is necessary to perform imaging. Thus, the MR isolette system 250 eliminates the need for the infant to undergo further handling and allows MRI to be performed repeatedly over a longer duration of time while the infant is positioned in MR isolette 200. As described in further detail below, MR isolette 200 can be slid out of the isocenter of MRI device 260 if access to the infant is needed. As a result, MR isolette system 250, which provides for coupling a standalone portable MRI device to an isolette, provides for extended care of the infant.

Figure 3A:
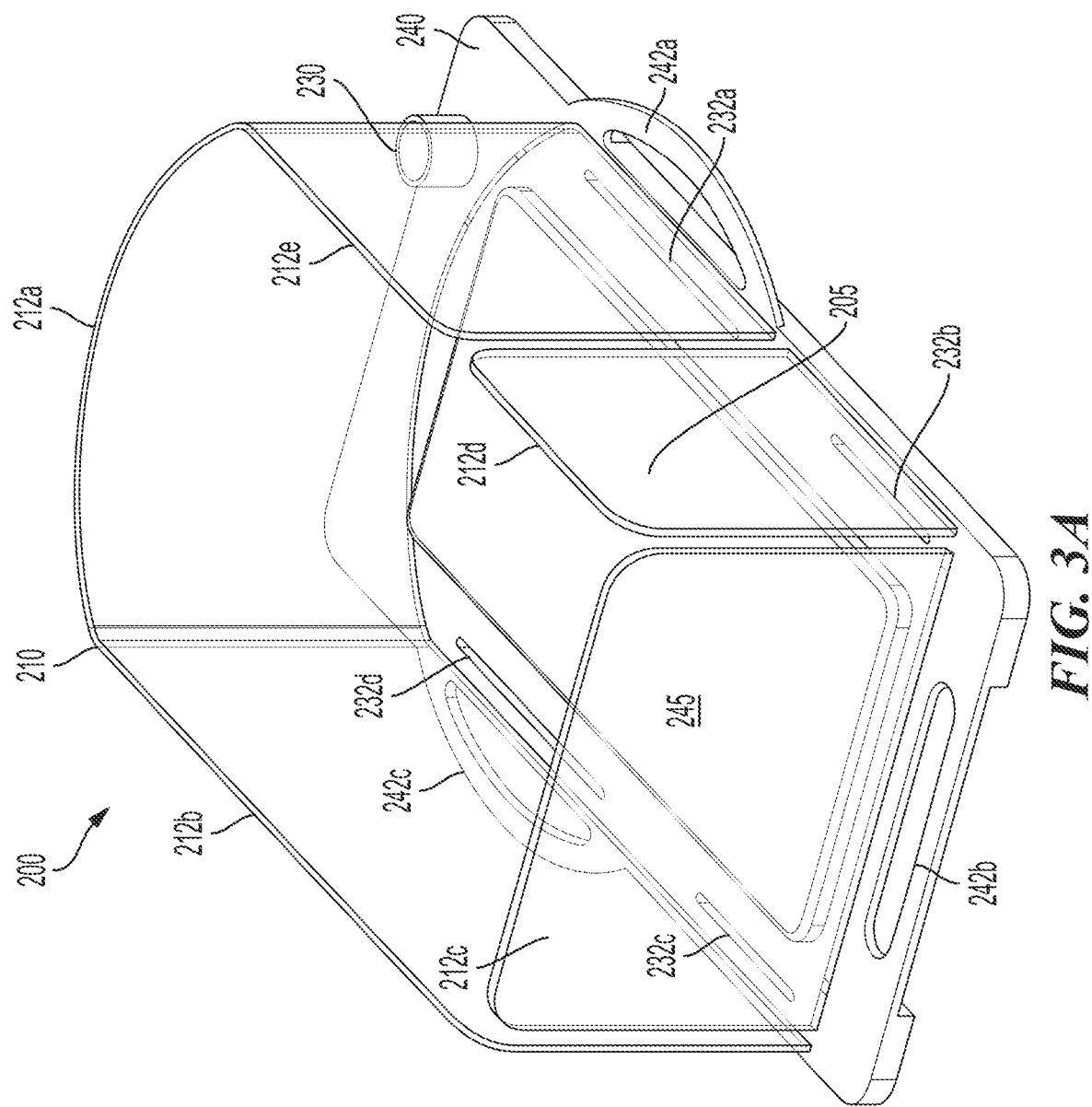
FIG. 3A illustrates a top perspective view of an MR isolette configured for use with an MRI device, in accordance with some embodiments of the technology described herein.
Figure 3B:
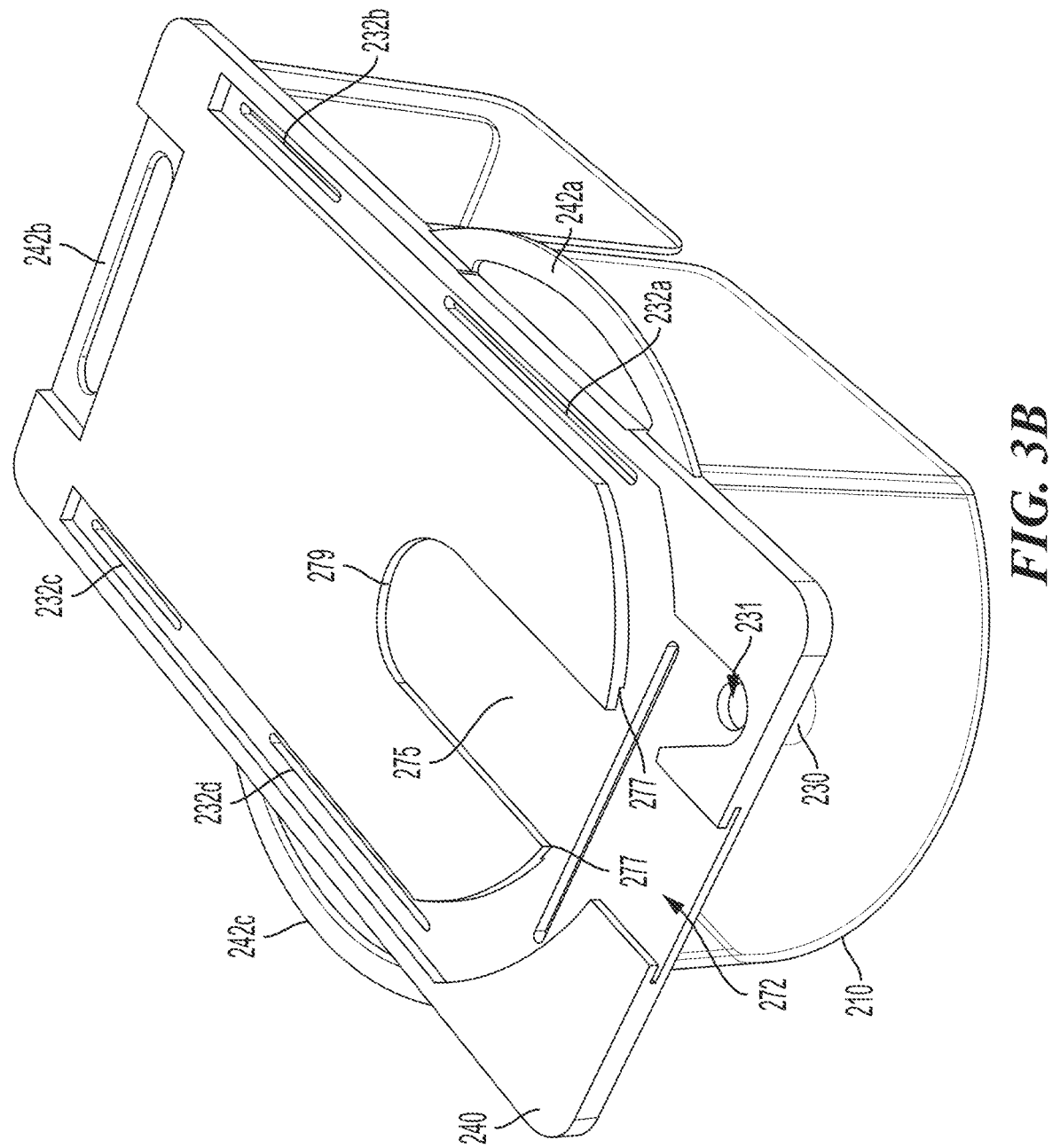
FIG. 3B illustrates a bottom perspective view of the MR isolette of FIG. 3A, in accordance with some embodiments of the technology described herein.

FIGS. 3A and 3B respectively illustrate top and bottom perspective views of an MR isolette 200 configured for use with an MRI device, in accordance with some embodiments. As shown in FIG. 3A, MR isolette 200 comprises a bassinet 205 having an enclosure 210, formed by walls 212a-e extending upwards from base 240, the base 240 supporting the enclosure 210. Walls 212a-e may be made from a transparent material that allows an infant positioned within the enclosure 210 to be visible through the walls 212a-e and during the entirety of image acquisition. In some embodiments, walls 212a-e comprise plastic. However, walls 212a-e may be made of any material that provides suitable visibility into the interior of the enclosure 210, as aspects of the technology described herein are not limited in this respect. One or more of walls 212a-e may be configured to be folded or removed to facilitate greater accessibility to the infant if needed. For example, slots or grooves (not shown) may be provided in base 240 into which one or more walls may be removably coupled such that the one or more walls can be inserted and removed as desired. Alternatively, one or more of walls 212a-e may be coupled to base 240 via a hinge that allows the respective wall to be folded down. For example, walls 212c and 212d may be removably or foldably coupled to base 240 to allow better accessibility for medical personnel. One or more of the walls of enclosure 210 may be attached to base 240 in a fixed manner without the ability to be removed, folded down or otherwise moved or detached. Alternatively, one or more of walls 212a-e may be coupled to another of walls 212a-e, for example, via a hinge that allows the respective wall to be folded inward and/or outward. Any number of the walls of enclosure 210 may be configured to provide accessibility and/or the enclosure may be provided in other ways to allow access to the infant (e.g., armholes may be provided through one or more of the walls to allow access to the infant).

MR isolette 200 further comprises an inlet 230 provided in base 240 to facilitate climate control for the interior of the MR isolette 200. In particular, inlet 230 allows a source of air to be connected to the MR isolette 200 to control the temperature and/or humidity of the infant's environment (for example, to maintain a constant temperature and/or humidity in the enclosure 210). Air provided to inlet 230 is circulated through the interior of the MR isolette 200 via one or more vents, for example, vents 232a-d provided in base 240 of MR isolette 200. As illustrated in the bottom-side view of MR isolette 200 in FIG. 3B, air flowing into inlet 230 is provided to the underside of the isolette via outlet 231 and enters enclosure 210 via vents 232a-d. Thus, inlet 230 and vents 232a-d allow for ducted air to be circulated through enclosure 210, thereby providing temperature and/or humidity control for MR isolette 200. In some embodiments, inlet 230 may be configured to allow current climate control fixtures to connect to the MR isolette so that MR isolette 200 can be used with existing temperature/humidity control equipment (e.g., temperature/humidity control equipment in an infant and/or neonatal intensive care unit).

In the illustrated embodiment, enclosure 210 has an open top such that an outlet for air in the enclosure 210 is provided over walls 212a-e. Furthermore, configuring enclosure 210 with an open top may facilitate easier positioning of an infant on base 240 of the MR isolette 200. However, in some embodiments, MR isolette 200 is configured having a cover disposed on top of the enclosure 210 and coupled to walls 212a-e. In such embodiments, the enclosure 210 may be configured having outlet vents to provide air circulation inside the enclosure 210 by venting internal air out of the enclosure 210. Furthermore, the cover may be removably coupled to the walls 212a-e (e.g., by one or more hinges, etc.) such that the cover can be removed when desired.

Base 240 of MR isolette 200 further comprises a padded surface 245 (e.g., a bed pad) on which the infant (e.g., a neonate) is placed. The padded surface 245 may be configured to increase comfort of the infant to reduce movement of the infant during image acquisition. According to some embodiments, the infant is first placed into an infant-carrying apparatus, such as infant-carrying apparatus 300 described herein, to facilitate transfer and handling of the infant (e.g., from a conventional isolette to the MR isolette 200), as described in further detail below in connection with FIGS. 4A-4B.

To facilitate transfer and positioning of MR isolette 200 (e.g., positioning MR isolette at least partially within an imaging region of an MRI device), handholds 242 are provided on the perimeter of base 240. For example, handholds 242a-c allow personnel to lift MR isolette 200 for carrying or transport and facilitating positioning of MR isolette 200 within the MRI device (e.g., sliding MR isolette 200 into and out of the isocenter of MRI device 260), as described in further detail below. In some embodiments, MR isolette 200 may be configured to rest on a frame (not shown), such as the frame 130 of FIG. 1, during periods in which the infant is not being imaged. The frame may be configured having wheels or another suitable conveyance mechanism to facilitate transport of the MR isolette 200 to different locations. When it is desired to perform imaging, MR isolette 200 may be moved from the frame and positioned in an imaging region of the MRI device, for example, MRI device 260 described herein, such that the infant need not be removed from the isolette 200 to perform imaging. In other embodiments, the infant may only be placed in the MR isolette 200 when imaging is to be performed, for example, by transferring the infant from a conventional isolette to the MR isolette 200. The MR isolette 200 may provide a controlled environment as well as providing for monitoring the infant during imaging such that the infant need not be returned to the conventional isolette between successive image acquisitions. Instead, the infant may remain in the MR isolette 200 and only return to the conventional isolette when image acquisition is completed, thus reducing the number of times the infant needs to be transported and exposed to an uncontrolled environment.

Figure 3C:
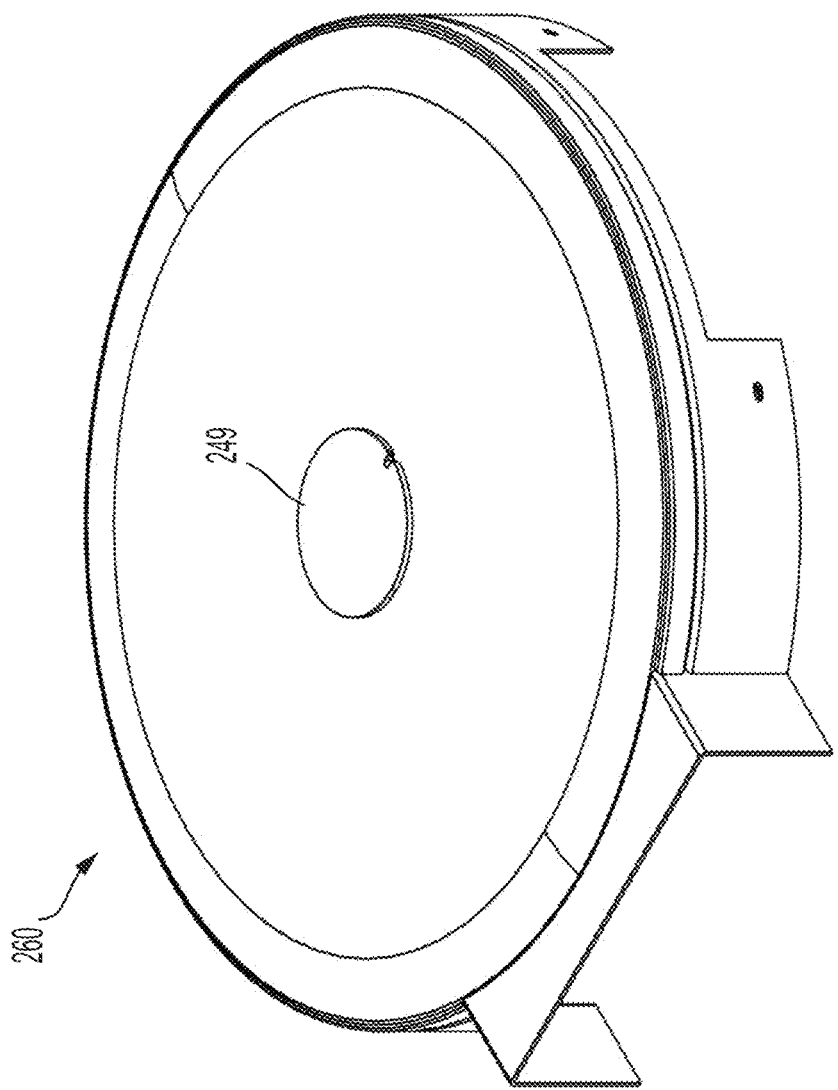
FIG. 3C illustrates a portion of an MRI device configured for coupling to the example MR isolette of FIG. 3B, in accordance with some embodiments of the technology described herein.

FIG. 3B illustrates a bottom view of the MR isolette 200 of FIG. 3A, in accordance with some embodiments of the technology described herein. In some embodiments, a bottom surface of the MR isolette 200 (e.g., the underside of base 240) may be configured to facilitate positioning of the MR isolette 200 relative to an MRI device, such as MRI device 260. For example, as shown in FIG. 3B, the underside of base 240 includes a recessed portion (e.g., inlet slot 272 and receptacle 275) for removably coupling MR isolette 200 to a complementary portion of the MRI device 260 (e.g., positioning member 249 of MRI device 260 illustrated in FIG. 3C). In particular, inlet slot 272 provides an opening for positioning member 249 to slide into receptacle 275 to couple MR isolette 200 to the MRI device 260. In some embodiments, the complementary portion of the MRI device may have wider dimensioned portions (e.g., one or more wing portions) which may be received in tracks 277 of the receptacle 275. Receptacle 275 may be dimensioned so that MR isolette 200 is positioned correctly within an imaging region of the MRI device 260 when the positioning member 249 enters all the way into receptacle 275 (i.e., when the positioning member 249 is seated within the cul-de-sac portion 279 at the end of receptacle 275). In this manner, MR isolette 200 may be placed on the MRI device 260 (e.g., on a platform such as bridge 285 illustrated in FIG. 1) and pushed into position within an imaging region of the MRI device 260 by sliding the positioning member 249 into receptacle 275 until the cul-de-sac portion 279 at the end of the receptacle 275 prevents further movement. In some embodiments, wider dimensioned portions (e.g., one or more wing portions of a complementary portion of the MRI device) may be received by the tracks 277. As shown in FIG. 3B, tracks 277 may comprise slotted portions for the one or more wider dimensioned portions to be received such that when a wider dimensioned portion is inserted into a track 277, vertical movement of the MR isolette 200 is prevented. Thus, the tracks 277 may prevent movement or inadvertent removal of the MR isolette 200 from the MRI device during imaging.

Once positioned, at will MRI scanning of the infant may be performed without further need to transfer, transport or handle the infant. In particular, the infant can remain in the MR isolette 200 for the entire duration in which the infant requires monitoring (e.g., throughout the infant's stay in the NICU). In this scenario, the MR isolette 200 replaces the conventional isolette as the controlled environment for the infant throughout the duration of the infant's stay in a particular care unit (e.g., the NICU). During this time, serial imaging of the infant may be performed to monitor the infant by positioning the MR isolette 200 into an imaging region of MRI device 260 without removing the infant from MR isolette 200, eliminating risky transfer, transport and handling of the infant each time MRI is performed. Specifically, at will serial scanning of infants can be performing while avoiding repeated transportation of the infant between a conventional isolette and the MRI device 260. Use of the MR isolette system 250 also facilitates real time monitoring of designated physiological signals of the infant, as described herein.

As described herein, the infant may be placed within an infant-carrying apparatus such as a wrap, or sling, to protect the infant during, for example, the initial transfer of the infant from a conventional isolette or other location to the MR isolette 200 and during the infant's stay in the MR isolette 200. For example, in some embodiments, the MR isolette system 250 further comprises an infant-carrying apparatus 300. Infant-carrying apparatus 300 may act as a cocoon for the infant during an MR scan to comfort the infant, reduce movement, and position the infant appropriately relative to an MRI device. The infant-carrying apparatus 300 may further comprise RF coils, as described herein, for imaging one or more portions of the infant's body.

Figure 4A:
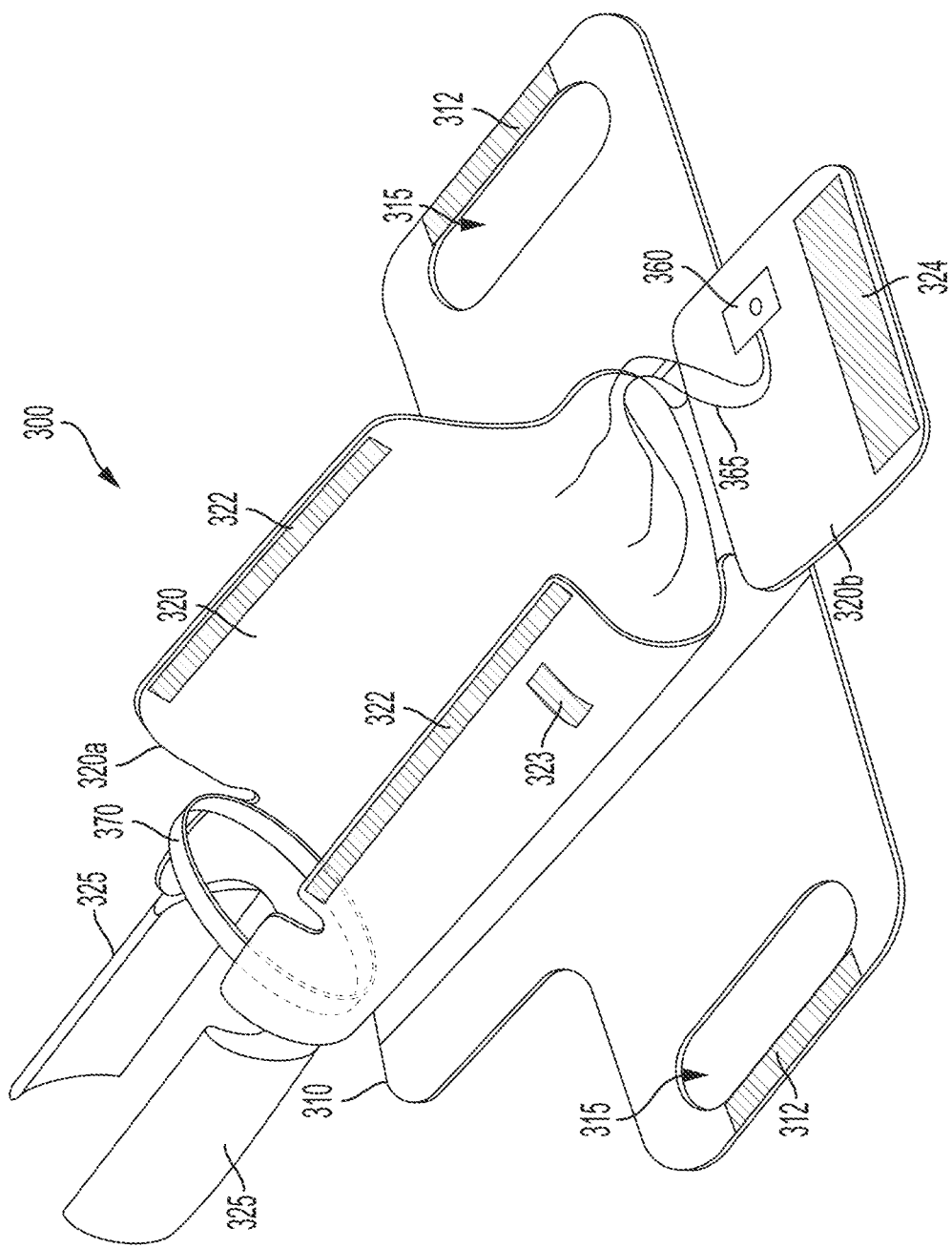
FIG. 4A illustrates an example infant-carrying apparatus in an open configuration, in accordance with some embodiments of the technology described herein.
Figure 4B:
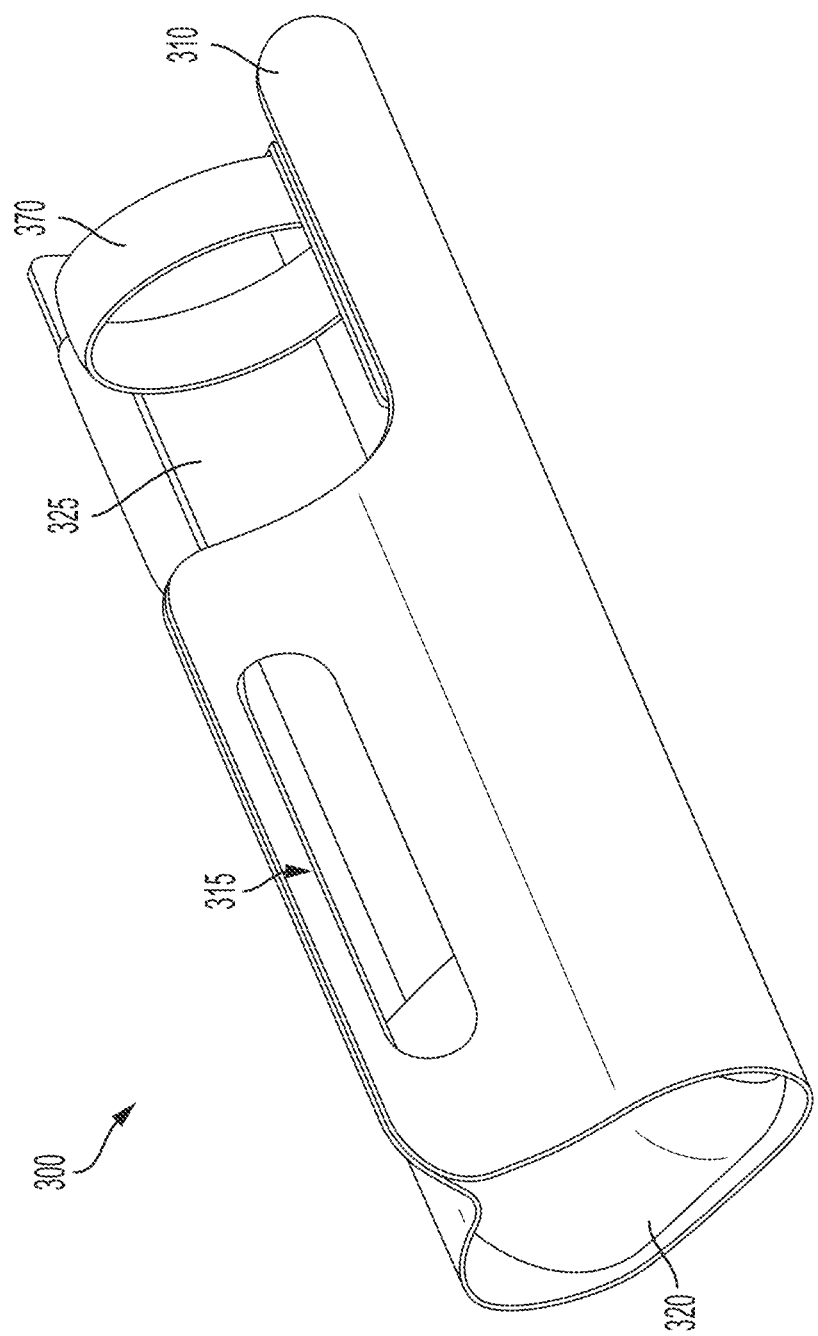
FIG. 4B illustrates the example infant-carrying apparatus of FIG. 4A in a closed configuration, in accordance with some embodiments of the technology described herein.

FIGS. 4A and 4B illustrate an example infant-carrying apparatus in open and closed configurations, respectively, in accordance with some embodiments of the technology described herein. In particular, FIG. 4A illustrates infant-carrying apparatus 300 in an open configuration. Infant-carrying apparatus may comprise an infant support configured for supporting the infant. In the illustrated embodiment, the infant support comprises a jacket 310 to support the infant's head and spine during transfer from a conventional isolette to a MR isolette, such as MR isolette 200. Jacket 310 comprises handholds 315 that come together and are secured with fasteners 312 (e.g., hook and loop fasteners, touch fasteners, snaps, or other suitable fasteners) coupling a left side of the jacket to a right side of the jacket to provide a handle to allow personnel to grip infant-carrying apparatus 300 securely during transfer and positioning of the infant.

Jacket 310 may be configured in any suitable manner for supporting the infant. For example, in some embodiments, infant support further comprises a padding coupled to the jacket. The padding may be part of the jacket, such as part of a single integral piece (e.g., by coupling the padding to the jacket in any suitable manner, or manufacturing the jacket out of a padded material). In some embodiments, the padding is separate from the jacket but coupled the jacket, e.g., on the interior of the jacket to form an interior sleeve disposed within the jacket. In the illustrated embodiment shown in FIGS. 4A-4B, the padding comprises an inner swaddle 320 disposed on the interior of the jacket 310 and configured to wrap the infant comfortably and securely during transfer. In such embodiments, jacket 310 may comprise a rigid material configured to support the infant's body and head during transfer. The jacket 310 may further comprise a material resistant to external contaminants which the infant may be exposed to during transfer which may otherwise compromise the infant's health (e.g., a water resistant material, etc.).

As shown in FIG. 4A, swaddle 320 includes a body wrap portion 320a arranged to wrap around the infant and secure with inner fasteners 322 and 323 to allow the infant to be tightly wrapped in the swaddle 320. Swaddle 320 also includes fold 320b arranged to close up the swaddle by securing fold 320b to body wrap portion 320a via fastener 324. Swaddle 320 may be secured to outer jacket 310 by any suitable means. For example, in some embodiments, swaddle 320 and outer jacket 310 are detachably coupled together using a fastener, such as a hook and loop fastener. In other embodiments, swaddle 320 may not be secured to outer jacket 310 at all, but is configured to be received by outer jacket 310 when the infant-carrying apparatus 300 is in a closed configuration.

In some embodiments, the infant-carrying apparatus 300 further comprises rods (not shown) configured to be positioned on opposing sides of an infant's spine when an infant is placed in the infant-carrying apparatus 300. In some embodiments, the rods may be part of the jacket 310. In some embodiments, the rods may be disposed between jacket 310 and swaddle 320. The rods may prevent sagging of the infant's spine and/or components of the infant-carrying apparatus 300 (e.g., the head coil 370, as described herein) during transport.

Fold 320b also accommodates and/or provides access to baby monitor leads 365 (shown partially in FIG. 4A), which may be secured to fold 320b. Baby monitor leads 365 may be coupled to electrodes placed on the infant's body on one end, and may be connected to an external device on another end. The baby monitor leads 365 may therefore facilitate continuous monitoring of the infant while the infant is positioned in the infant-carrying apparatus 300. A strain relief 360 may further be provided on fold 320b for baby monitor leads 365 to accommodate movement of the infant and/or infant-carrying apparatus while preventing breakage of the leads 365.

As shown in FIG. 4A, infant-carrying apparatus 300 further comprises head pads 325 for supporting the infant's head while the infant is positioned in the infant-carrying apparatus 300. Head pads 325 may be made of any suitable material for supporting the infant's head, for example, a foam material, such that the infant remains comfortable while positioned in the infant-carrying apparatus 300. The head pads 325 of the infant-carrying apparatus 300 may be removably coupled to the infant-carrying apparatus 300. For example, the infant can be positioning in the swaddle 320, and head pads 325 can thereafter be placed on sides of the infant's head. In some embodiments, the head pads 325 may be positioned in the infant-carrying apparatus 300 prior to positioning the infant in the infant-carrying apparatus 300, as aspects of the technology are not limited in this respect. In some embodiments, head pads 325 are further configured to provide acoustic dampening to mitigate the acoustic noise generated by MR pulse sequences during image acquisition.

As described herein, the infant-carrying apparatus 300 may be configured to enable imaging of one of more portions of an infant's body. For example, as shown in FIG. 4A, infant-carrying apparatus 300 further comprises a head coil 370 coupled to and/or integrated with the infant-carrying apparatus 300 (e.g., coupled to and/or integrated with the infant support). The head coil 370 can be configured to detect MR signals during imaging performed by the MRI device. In some embodiments, the head coil 370 may be further configured to transmit RF pulses according to one or more pulse sequences during imaging performed by the MRI device. Transmit and receive coils, often referred to as radio frequency (RF) coils, of an MRI device, such as head coil 370, for example, may be configured as separate coils for transmitting and receiving, multiple coils for transmitting and/or receiving, or the same coils for transmitting and receiving. Thus, a transmit/receive component may include one or more coils for transmitting, one or more coils for receiving, and/or one or more coils for transmitting and receiving. Transmit/receive coils are also often referred to as Tx/Rx or Tx/Rx coils to generally refer to the various configurations for the transmit and receive magnetics components of an MRI device. These terms are used interchangeably herein.

In the illustrated embodiment in FIGS. 4A-4B, head coil 370 is a receive-only coil (e.g., the head coil is configured only to detect MR signals during MR imaging but is not configured to transmit RF pulses). Head coil 370 comprises a flexible loop which encompasses the infant's head such that imaging of the infant's head can be performed when the infant is positioned within an MRI device, such as MRI device 260. For example, MRI device may contain components for performing MR imaging, for example, components for generating a main $B_0$ magnetic field, components for generating gradient fields, and/or components for generating transmit RF pulses and/or detecting MR signals, as described herein. The head coil 370 may be used in combination with the components of the MRI device to perform imaging of an infant positioned in a MR isolette. In addition, the head coil 370 may be electronically coupled to the MRI device. For example, the MRI device may comprise one or more power components configured to provide power to the MRI device for performing image acquisition, as described herein, and the head coil 370 may be electronically coupled to at least one power component configured to provide power to the head coil 370.

Although, in the illustrated embodiment, the infant-carrying apparatus 300 is configured having components for performing MR imaging of an infant's head (e.g., head coil 370), the infant-carrying apparatus 300 may be configured having components for additionally or alternatively imaging other portions of the infant's body, for example, a body coil (not shown) for imaging the infant's spine. Additional imaging components of the infant-carrying apparatus 300, such as a body coil, may be configured in any suitable manner. For example, a body coil may be configured to transmit RF pulses and/or detect MR signals (e.g., as a Tx/Rx coil) to facilitate imaging of the infant's body. In some embodiments, the infant-carrying apparatus 300 is configured having a transmit and receive body coil and a receive-only head coil. In some embodiments, the infant-carrying apparatus 300 is configured having only a head coil and the head coil is configured to both transmit RF pulses and detect MR signals during MR imaging.

FIG. 4B illustrates the example infant-carrying apparatus of FIG. 4A in a closed configuration, in accordance with some embodiments of the technology described herein. As shown in FIG. 4B, the jacket 310 and swaddle 320 are in closed and fastened positions and ready for transport. Head pads 325 are shown positioned adjacent to head coil 370. In some embodiments, head pads 325 are disposed adjacent to an exterior of head coil 370 such that the head coil 370 is disposed between an infant's head and the head pads 325. In other embodiments, the head pads 325 are disposed between the infant's head and the head coil 370.

A method for acquiring an MR image of an infant may begin with the infant being positioned in a conventional isolette (such as isolette 100 shown in FIG. 1, for example), with the infant-carrying apparatus 300 being positioned underneath the infant's back, and the head being positioned in the head coil 370 of the infant-carrying apparatus 300 (e.g., by positioning the infant on the infant support of the infant-carrying apparatus such that the infant's head is at least partially encircled by the head coil 370). In some embodiments, the infant-carrying apparatus 300 may additionally or alternatively include at least one RF body coil, and the method may further comprise positioning the infant on the infant support of the infant-carrying apparatus such that the infant's body is at least partially encircled by the at least one RF body coil. Next, the infant is wrapped (e.g., with excess textile material flaps, such as body and fold portions 320a, 320b of swaddle with fasteners 322-324) to be snug. The infant-carrying apparatus 300 and infant may be further secured by closing outer jacket 310 of the infant-carrying apparatus 300 using fasteners 312 (e.g., by coupling left and right sides of the jacket). Finally, a clinician gathers the two cut-out hand holds 315, so the infant-carrying apparatus 300 can be lifted from the conventional isolette and be transported to a POC MRI device, such as MRI device 260. For example, the infant can be lifted, using the infant-carrying apparatus 300, and placed in a MR isolette, such as MR isolette 200 (for example between raised portions 420, described herein). The infant-carrying apparatus 300 also serves to properly guide the cables (e.g., baby monitor leads 365) of various physiological sensors so they can be reconnected when the infant is positioned in the MR isolette.

At the POC MRI, the cables of the RF coil(s) may be coupled to the POC MRI and the physiological sensor cables may be coupled to the local monitors. At least a part of the infant may be positioned within an imaging region of the MRI device by removably coupling the MR isolette to the MRI device (e.g., by inserting a positioning mechanism of the MRI device into receptacle 275 of the MR isolette). After positioning at least a part of the infant into the imaging region of the MRI device, one or more magnetic resonance images may be obtained. In some embodiments, multiple magnetic resonance images are obtained before removing the infant from the imaging region of the MRI device. The inventors have recognized that at-will serial scanning of an infant using the MRI device is possible using the MR isolette described herein as the infant can remain in a controlled environment for the duration of imaging, without the need to return the infant to a conventional isolette after each image acquisition. After the scan is finished, the infant can be removed from the imaging region by decoupling the MR isolette from the MRI device. All or some of the cables of the infant-carrying apparatus may be unplugged, and the infant-carrying apparatus 300 may be removed from the MR isolette and returned to a conventional isolette or another location. Thereafter, the infant may be unbundled from the infant-carrying apparatus 300 and the sensor cables are reconnected to the monitoring devices.

Thus, aspects of the infant-carrying apparatus described herein allow for simple transport of an infant between a conventional isolette and a POC MRI device and vice versa. In some embodiments, the infant-carrying apparatus may be used to transport an infant between a conventional isolette and a MR isolette, such as MR isolette 200 described herein. The infant-carrying apparatus further allows positioning of an integrated RF coil of the apparatus (e.g., head coil 370) in the isocenter of a POC MRI device. In addition, the infant-carrying apparatus allows orderly transport of the cables coming off the physiological monitor sensors attached to the infant between a conventional isolette and POC MRI to be connected with the appropriate monitoring devices at either location (the conventional isolette or the POC MRI device).

Figure 5:
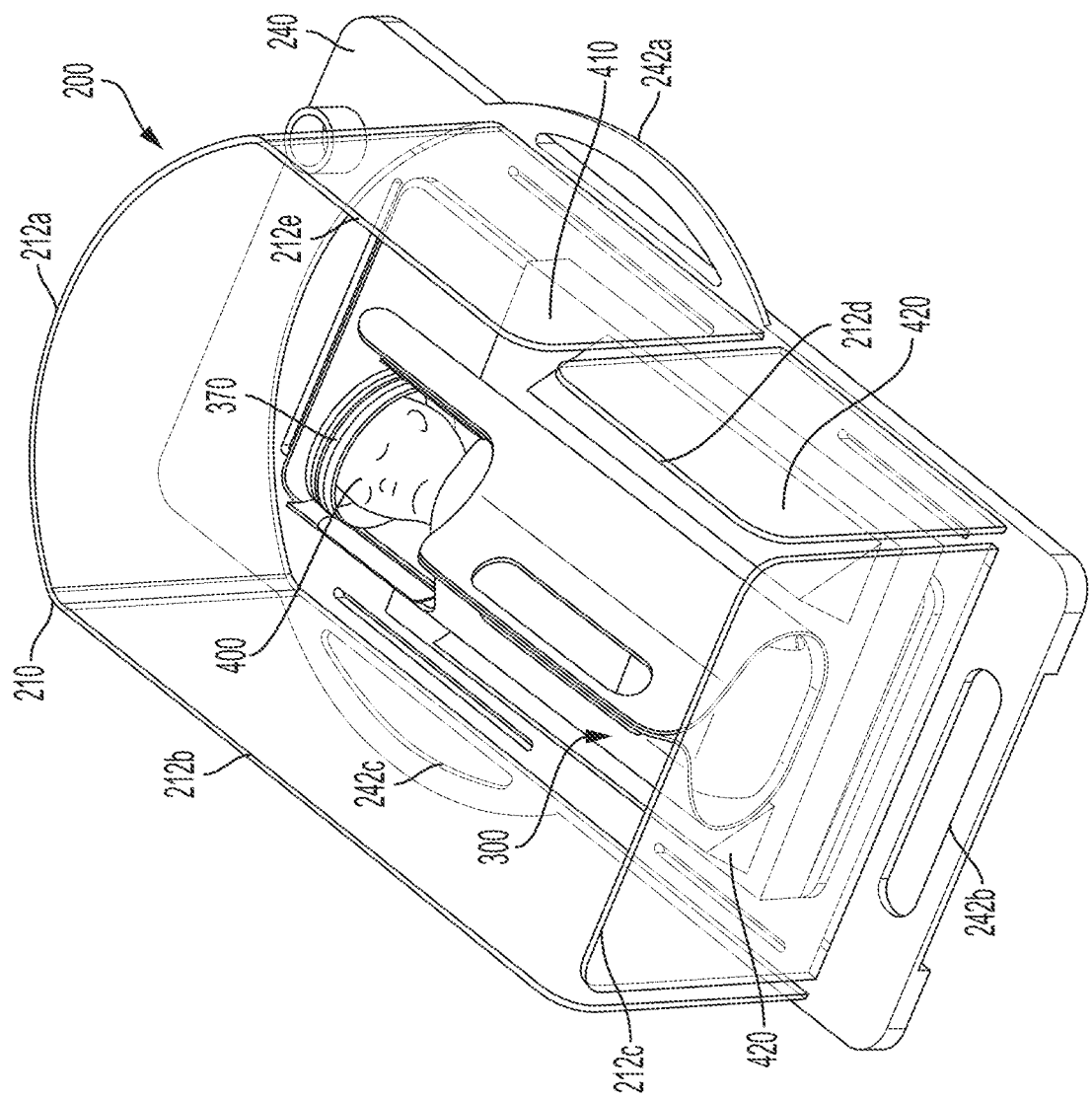
FIG. 5 illustrates the example MR isolette system of FIG. 2, with the example MR isolette of FIG. 3A having the infant-carrying apparatus of FIG. 4A and an infant disposed therein, in accordance with some embodiments of the technology described herein.

FIG. 5 illustrates the MR isolette system of FIG. 2, with the example MR isolette of FIG. 3A having the infant-carrying apparatus of FIG. 4A and an infant disposed therein, in accordance with some embodiments of the technology described herein. For example, as shown in FIG. 5, an infant 400 can be secured in infant-carrying apparatus 300, and infant-carrying apparatus 300 can be positioned in MR isolette 200 for MR imaging. In the illustrated embodiment, a padding 410 is positioned between infant-carrying apparatus 300 and base 240 of the MR isolette 200 such that the infant is vertically positioned at the isocenter of an imaging region when the MR isolette 200 is positioned in an MRI device, such as MRI device 260 described herein. Padding 410 may be made of any suitable material, for example, a non-ferrous material (e.g., a foam, etc.).

In the illustrated embodiment, the padding 410 comprises raised portions 420 disposed on either side of the padding 410 such that infant-carrying apparatus 300 and infant 400 can be positioned between the raised portions 420. Raised portions 420 may be configured to secure infant 400 and the infant-carrying apparatus 300, and prevent inadvertent movement of infant 400 during imaging and transport, including preventing the infant 400 from falling off the padding 410 and/or the MR isolette 200. Although in the illustrated embodiment, the raised portions 420 are configured as triangular shaped wedges, in other embodiments, the padding 410 may comprise additional or alternative elements for securing the infant 400 on the padding 410 having any suitable shape (e.g., rectangular-shaped, semi-cylindrical-shaped, etc.). Furthermore, raised portions 420 may comprise any suitable material, e.g., a soft material such as foam.

As described herein, the MR isolette and infant-carrying apparatus can facilitate transport, positioning, and monitoring of an infant in an imaging region of an MRI device while maintaining the infant in a controlled environment. Aspects of example MRI devices will thus be described herein. For example, FIG. 6 is a block diagram of some components of an example MRI device 260. In the illustrative example of FIG. 6, MRI device 260 comprises computing device 604, controller 606, pulse sequences store 608, power management system 610, and magnetics components 620. It should be appreciated that system 260 is illustrative and that an MRI device may have one or more other components of any suitable type in addition to or instead of the components illustrated in FIG. 6. However, an MRI device will generally include these high level components, though the implementation of these components for a particular MRI device may differ vastly, as described in further detail below.

As illustrated in FIG. 6, magnetics components 620 comprise $B_0$ magnet 265, shim coils 624, RF transmit and receive coils 626, and gradient coils 628. Magnet 265 may be used to generate the main magnetic field $B_0$. Magnet 265 may be any suitable type or combination of magnetics components that can generate a desired main magnetic $B_0$ field. As described above, in the high field regime, the $B_0$ magnet is typically formed using superconducting material generally provided in a solenoid geometry, requiring cryogenic cooling systems to keep the $B_0$ magnet in a superconducting state. Thus, high-field $B_0$ magnets are expensive, complicated and consume large amounts of power (e.g., cryogenic cooling systems require significant power to maintain the extremely low temperatures needed to keep the $B_0$ magnet in a superconducting state), require large dedicated spaces, and specialized, dedicated power connections (e.g., a dedicated three-phase power connection to the power grid). Conventional low-field $B_0$ magnets (e.g., $B_0$ magnets operating at 0.2 T) are also often implemented using superconducting material and therefore have these same general requirements. Other conventional low-field $B_0$ magnets are implemented using permanent magnets, which to produce the field strengths to which conventional low-field systems are limited (e.g., between 0.2 T and 0.3 T due to the inability to acquire useful images at lower field strengths), need to be very large magnets weighing 5-20 tons. Thus, the $B_0$ magnet of conventional MRI devices alone prevents both portability and affordability.

Gradient coils 628 may be arranged to provide gradient fields and, for example, may be arranged to generate gradients in the $B_0$ field in three substantially orthogonal directions (X, Y, Z). Gradient coils 628 may be configured to encode emitted MR signals by systematically varying the $B_0$ field (the $B_0$ field generated by magnet 265 and/or shim coils 624) to encode the spatial location of received MR signals as a function of frequency or phase. For example, gradient coils 628 may be configured to vary frequency or phase as a linear function of spatial location along a particular direction, although more complex spatial encoding profiles may also be provided by using nonlinear gradient coils. For example, a first gradient coil may be configured to selectively vary the $B_0$ field in a first (X) direction to perform frequency encoding in that direction, a second gradient coil may be configured to selectively vary the $B_0$ field in a second (Y) direction substantially orthogonal to the first direction to perform phase encoding, and a third gradient coil may be configured to selectively vary the $B_0$ field in a third (Z) direction substantially orthogonal to the first and second directions to enable slice selection for volumetric imaging applications. As described above, conventional gradient coils also consume significant power, typically operated by large, expensive gradient power sources, as described in further detail below.

MRI is performed by exciting and detecting emitted MR signals using transmit and receive coils, respectively (often referred to as radio frequency (RF) coils). As described herein, transmit/receive coils of an MRI device may include separate coils for transmitting and receiving, multiple coils for transmitting and/or receiving, or the same coils for transmitting and receiving. Thus, a transmit/receive component may include one or more coils for transmitting, one or more coils for receiving and/or one or more coils for transmitting and receiving. Transmit/receive coils are also often referred to as Tx/Rx or Tx/Rx coils to generically refer to the various configurations for the transmit and receive magnetics component of an MRI device. These terms are used interchangeably herein. In FIG. 6, RF transmit and receive coils 626 comprise one or more transmit coils that may be used to generate RF pulses to induce an oscillating magnetic field Bi. The transmit coil(s) may be configured to generate any suitable types of RF pulses. As described herein, the infant-carrying apparatus 300 may comprise at least one RF coil coupled and/or integrated with the apparatus to facilitate MR imaging. For example, at least one transmit coil of the MRI device is configured to transmit RF pulses according to one or more pulse sequences during MR imaging while the at least one RF coil of the infant-carrying apparatus may be configured to detect MR signals during MR imaging. Thus, the transmit and receive coils of the infant-carrying apparatus and MRI device may work in combination to perform MR imaging.

Power management system 610 includes electronics to provide operating power to one or more components of the low-field MRI device 260. For example, as described in more detail below, power management system 610 may include one or more power supplies, gradient power components, transmit coil components, and/or any other suitable power electronics needed to provide suitable operating power to energize and operate components of MRI device 260. As illustrated in FIG. 6, power management system 610 comprises power supply 612, power component(s) 614, transmit/receive switch 616, and thermal management components 618 (e.g., cryogenic cooling equipment for superconducting magnets). Power supply 612 includes electronics to provide operating power to magnetic components 620 of the MRI device 260. For example, power supply 612 may include electronics to provide operating power to one or more $B_0$ coils (e.g., $B_0$ magnet 265) to produce the main magnetic field for the low-field MRI device. Transmit/receive switch 616 may be used to select whether RF transmit coils or RF receive coils are being operated.

Power component(s) 614 may include one or more RF receive (Rx) pre-amplifiers that amplify MR signals detected by one or more RF receive coils (e.g., coils 626), one or more RF transmit (Tx) power components configured to provide power to one or more RF transmit coils (e.g., coils 626), one or more gradient power components configured to provide power to one or more gradient coils (e.g., gradient coils 628), and one or more shim power components configured to provide power to one or more shim coils (e.g., shim coils 624).

In conventional MRI devices, the power components are large, expensive and consume significant power. Typically, the power electronics occupy a room separate from the MRI scanner itself. The power electronics not only require substantial space, but are expensive complex devices that consume substantial power and require wall mounted racks to be supported. Thus, the power electronics of conventional MRI devices also prevent portability and affordability of MRI.

As illustrated in FIG. 6, MRI device 260 includes controller 606 (also referred to as a console) having control electronics to send instructions to and receive information from power management system 610. Controller 606 may be configured to implement one or more pulse sequences, which are used to determine the instructions sent to power management system 610 to operate the magnetic components 620 in a desired sequence (e.g., parameters for operating the RF transmit and receive coils 626, parameters for operating gradient coils 628, etc.). As illustrated in FIG. 6, controller 606 also interacts with computing device 604 programmed to process received MR data. For example, computing device 604 may process received MR data to generate one or more MR images using any suitable image reconstruction process(es). Controller 606 may provide information about one or more pulse sequences to computing device 604 for the processing of data by the computing device. For example, controller 606 may provide information about one or more pulse sequences to computing device 604 and the computing device may perform an image reconstruction process based, at least in part, on the provided information. In conventional MRI devices, computing device 604 typically includes one or more high performance work-stations configured to perform computationally expensive processing on MR data relatively rapidly. Such computing devices are relatively expensive equipment on their own.

As should be appreciated from the foregoing, currently available clinical MRI devices (including high-field, midfield and low-field systems) are large, expensive, fixed installations requiring substantial dedicated and specially designed spaces, as well as dedicated power connections. As described above, the inventors have developed low power, portable low-field MRI devices that can be deployed in virtually any environment and that can be brought to the patient who will undergo an imaging procedure. In this way, patients in emergency rooms, intensive care units, operating rooms and a host of other locations can benefit from MRI in circumstances where MRI is conventionally unavailable. The exemplary portable MRI devices described below in connection with FIGS. 7A, 7B and 8 are capable of being moved to locations at which MRI is needed (e.g., emergency and operating rooms, primary care offices, neonatal units, intensive care units, specialty departments, hospital rooms, recovery units, etc.), facilitating point-of-care MRI operable in proximity to standard hospital equipment such as hospital beds, wheelchairs, other medical devices, computing equipment, life support systems, etc. Additionally, the exemplary portable MRI devices described herein, allow for the deployment of the MRI device in virtually any location so that a patient can be easily brought to the MRI device (e.g., transported using a standard hospital bed or wheelchair, or, in some cases, by a portable isolette) to achieve point-of-care MRI. For example, in some cases, the portable MRI device may be transported to a neonatal and/or infant intensive care unit to provide for imaging of infants, and infants may be transported from a conventional isolette into a MR isolette, for example, via an infant-carrying apparatus, and the MR isolette can be positioned in an imaging region of the MRI device to facilitate imaging.

FIGS. 7A and 7B illustrate an example MRI device, in accordance with some embodiments of the technology described herein. In the illustrated embodiments, MRI device 260 is a low power, portable low-field MRI device. Portable MRI device 260 comprises a $B_0$ magnet 265 including at least one first permanent magnet 265a and at least one second permanent magnet 265b magnetically coupled to one another by a ferromagnetic yoke 720 configured to capture and channel magnetic flux to increase the magnetic flux density within the imaging region (field of view) of the MRI device. $B_0$ magnet 265 may be encased or enclosed in a housing 712 along with one or more other magnetics components, such as the system's gradient coils (e.g., x-gradient, y-gradient and z-gradient coils) and/or any shim components (e.g., shim coils or permanent magnetic shims), $B_0$ correction coils, etc.

$B_0$ magnet 265 may be coupled to or otherwise attached or mounted to base 280 by a positioning mechanism 790, such as a goniometric stage (examples of which are described in the '434 patent), so that the $B_0$ magnet 265 can be tilted (e.g., rotated about its center of mass) to provide an incline to accommodate a patient's anatomy as needed. In FIG. 7A, the $B_0$ magnet 265 is shown level without an incline and, in FIG. 7B, the $B_0$ magnet 265 is shown after undergoing a rotation to incline the surface supporting the patient's anatomy being scanned. Positioning mechanism 790 may be fixed to one or more load bearing structures of base 280 arranged to support the weight of $B_0$ magnet 265. In addition to providing the load bearing structures for supporting the $B_0$ magnet, base 280 also includes an interior space configured to house the electronics 770 needed to operate the portable MRI device 1260 (e.g., one or more power components to operate the gradient coils, RF transmit/receive coils, RF coil amplifiers, power supplies, console, power distribution unit and other electronics needed to operate the MRI device).

According to some embodiments, the electronics 770 needed to operate portable MRI device 260 consume less than 1 kW of power, in some embodiments, less than 750 W of power and, in some embodiments, less than 500 W of power (e.g., MRI devices utilizing a permanent $B_0$ magnet solution). Example portable MRI device 260 illustrated in FIGS. 7A and 7B may be powered via a single power connection 775 configured to connect to a source of mains electricity, such as an outlet providing single-phase power (e.g., a standard or large appliance outlet), increasing the availability of the MRI device and the circumstances and locations in which the portable MRI device may be used.

Portable MRI device 260 illustrated in FIGS. 7A and 7B also comprises a conveyance mechanism 780 that allows the portable MRI device to be transported to different locations, for example, to an infant and/or neonatal intensive care unit. According to some embodiments, conveyance mechanism comprises a motor 786 coupled to drive wheels 784. Conveyance mechanism 780 may also include a plurality of castors 782 to assist with support and stability as well as facilitating transport. According to some embodiments, conveyance mechanism 780 includes motorized assistance controlled using a controller (e.g., a joystick or other controller that can be manipulated by a person) to guide the portable MRI device during transportation to desired locations. For example, rail 755 of base 280 illustrated in FIGS. 7A and 7B may be configured to detect when force is applied to the rail (e.g., by personnel pushing on the rail) and engage the conveyance mechanism to provide motorized assistance to drive the wheels in the direction of the applied force.

Portable MRI device 260 includes slides 760 that provide electromagnetic shielding to the imaging region of the system. According to some embodiments, slides 760 may also be formed by a conductive mesh providing shielding 765 to the imaging region and promoting a sense of openness for the system. Thus, slides 760 may provide electromagnetic shielding that is moveable to allow a patient to be positioned within the system, permitting adjustment by personnel once a patient is positioned or during acquisition, and/or enabling a surgeon to gain access to the patient, etc.

According to some embodiments, a portable MRI device does not include slides, providing for a substantially open imaging region, facilitating easier placement of a patient within the system, reducing the feeling of claustrophobia and/or improving access to the patient positioned within the MRI device (e.g., allowing a physician or surgeon to access the patient before, during or after an imaging procedure without having to remove the patient from the system) as shown, for example, in FIG. 8. MRI device 800 may comprise a $B_0$ magnet 822 that includes at least one first magnet 822a and at least one second magnet 822b magnetically coupled to one another by a ferromagnetic yoke 820 configured to capture and channel magnetic flux to increase the magnetic flux density within the imaging region (field of view) of the MRI device. MRI device 800 further comprises gradient coils 828a and 828b to provide X-gradient, Y-gradient and Z-gradient coils for spatial encoding of MR signals. $B_0$ magnet 822 may be coupled to or otherwise attached or mounted to base 850 to support the $B_0$ magnet. Base 850 includes housing 802 configured to house the electronics needed to operate the portable MRI device 800 (e.g., as described in detail in the '434 patent). To facilitate transporting the system to the point of care, for example, to an infant and/or neonatal intensive care unit, MRI device 800 may include a conveyance mechanism (e.g., wheels or castors 882).

The MRI devices described herein may have a maximum horizontal width W that facilitates the maneuverability of the system within the facilities in which the MRI device is used. According to some embodiments, the maximum horizontal dimension of a portable MRI device is in a range between 40 and 60 inches and, in some embodiments, in a range between 35 and 45 inches. For example, exemplary MRI device 800 has a maximum horizontal width of approximately 40 inches. MRI device 800 also includes bridge 873 that is mounted to the MRI device 800 to facilitate positioning a patient within the imaging region of the MRI device 800 (e.g., being configured to support at least a portion of MR isolette 200). Bridge 873 may be configured to be attached to different locations around the base to allow a patient to be positioned within the imaging region from different directions and/or orientations. According to some embodiments, bridge 873 is attached to the MRI device 800 so that it can be moved around the perimeter of the $B_0$ magnet. In some embodiments, bridge 873 is configured to be removed and reattached at different locations around the perimeter of the $B_0$ magnet. According to some embodiments, the bridge may be configured to attach to yoke 820, base 850 or any other suitable portion of MRI device 800, as the aspects are not limited in this respect.

The weight of the $B_0$ magnet is a significant portion of the overall weight of the MRI device which, in turn, impacts the portability of the MRI device. In embodiments that primarily use low carbon and/or silicon steel for the yoke and shimming components, an exemplary $B_0$ magnet dimensioned similar to that described in the foregoing may weigh approximately 550 kilograms. According to some embodiments, cobalt steel (CoFe) may be used as the primary material for the yoke (and possibly the shim components), potentially reducing the weight of $B_0$ magnet to approximately 450 Kilograms. According to some embodiments, the total weight of a portable MRI device is less than 1,500 pounds and, preferably, less than 1000 pounds to facilitate maneuverability of the MRI device.

$B_0$ magnets of the MRI devices described herein may be configured to produce a $B_0$ magnetic field in the very low field strength regime (e.g., less than or equal to approximately 0.2 T, 0.1 T, 50 mT, 20 mT, etc. or any field strength equal to or within the ranges listed herein). For example, a portable MRI device may be configured to operate at a magnetic field strength of approximately 64 mT, though any low-field strength may be used. $B_0$ magnetic field strengths in the very low-field regime facilitate a 5-Gauss line (e.g., the perimeter outside of which the fringe magnetic field from the $B_0$ magnet is 5 Gauss or less) that remains close to the portable MRI device. For example, according to some embodiments, the 5-Gauss line has a maximum dimension of less than seven feet and, more preferably, less than 5 feet and, even more preferably, less than 4 feet. In addition to using very low field strengths, shielding may be provided to reduce the volume of the region inside the 5-Gauss line.

The exemplary low-field MRI devices described above and in the '434 patent can be used to provide point-of-care MRI, either by bringing the MRI device directly to the patient or bringing the patient to a relatively nearby MRI device (e.g., by wheeling an infant to the MRI device via an isolette, etc.). For example, the portable MRI devices described herein may be transported to the point-of-care, such as an infant and/or neonate intensive care unit, eliminating the need to transport the infant to a specially shielded MR room.

The MRI devices described herein may be used in conjunction with aspects of the infant-carrying apparatus and MR isolette to facilitate imaging of infants in a controlled manner. For example, aspects of the infant-carrying apparatus described herein allow for secure and efficient transport of an infant between a conventional isolette and a MR isolette while also facilitating orderly transport of cables (e.g., leads) of any physiological monitor sensors connected to the infant. The infant-carrying apparatus also facilitates imaging one or more portions of the infants body via integrated coils (e.g., an integrated RF head coil). The MR isolette described herein can be positioned in an imaging region of the MRI device while providing a controlled environment, for example, by maintaining a climate controlled enclosure, in which the infant is positioned during imaging. As the MR isolette provides a controlled environment for the infant, the infant can remain in the MR isolette for the duration of image acquisition, thus minimizing the number of times the infant must be transported between the MR device and a conventional isolette and the length of time the infant spends outside of a controlled environment. Together, the infant-carrying apparatus and MR isolette assembly further facilitate positioning of the infant in the isocenter of the imaging region of the MRI device such that clinically useful MR images can be acquired. In some embodiments, a system comprises an MRI device, an infant-carrying apparatus, and a MR isolette.

Figure 9:
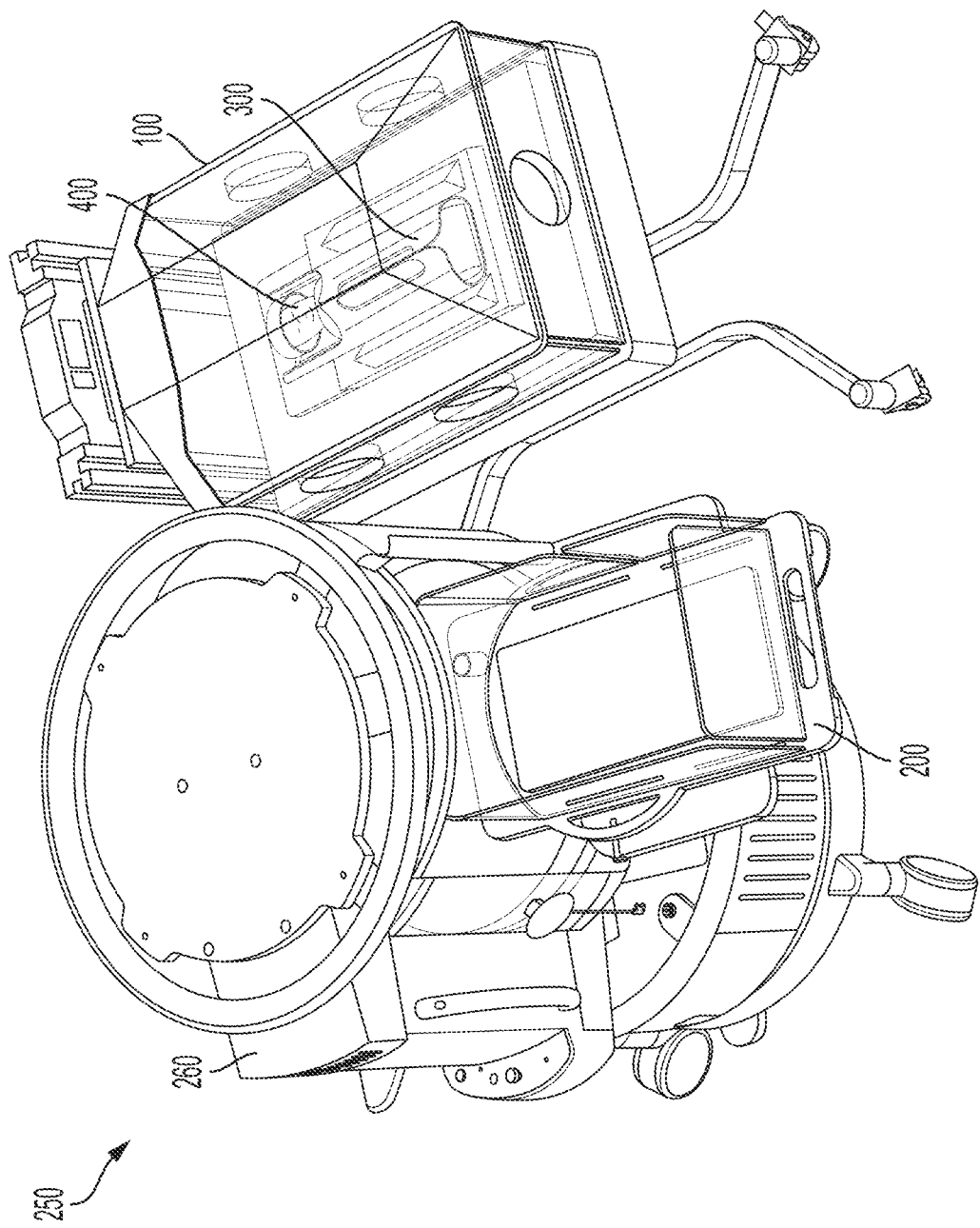
FIG. 9 illustrates an example MR isolette system configured to facilitate imaging of an infant using an MRI device, in accordance with some embodiments of the technology described herein.

FIGS. 9-11B illustrate aspects of transporting and positioning an infant relative to an MRI device. For example, FIG. 9 illustrates an example MR isolette system configured to facilitate MR imaging of an infant using an MRI device, in accordance with some embodiments of the technology described herein. As shown in FIG. 9, a process for positioning an infant relative to an MRI device 250 may begin with the infant 400 being positioned in a conventional isolette 100. To transport the infant 400 to the MR isolette 200, the infant may be positioned in infant-carrying apparatus 300, as described herein. As the MRI device 260 may be portable, in some embodiments, the MRI device 260 may be transported from another location to the conventional isolette 100, such that transporting the infant from the conventional isolette 100 to the MR isolette 200 is made simpler.

Figure 10:
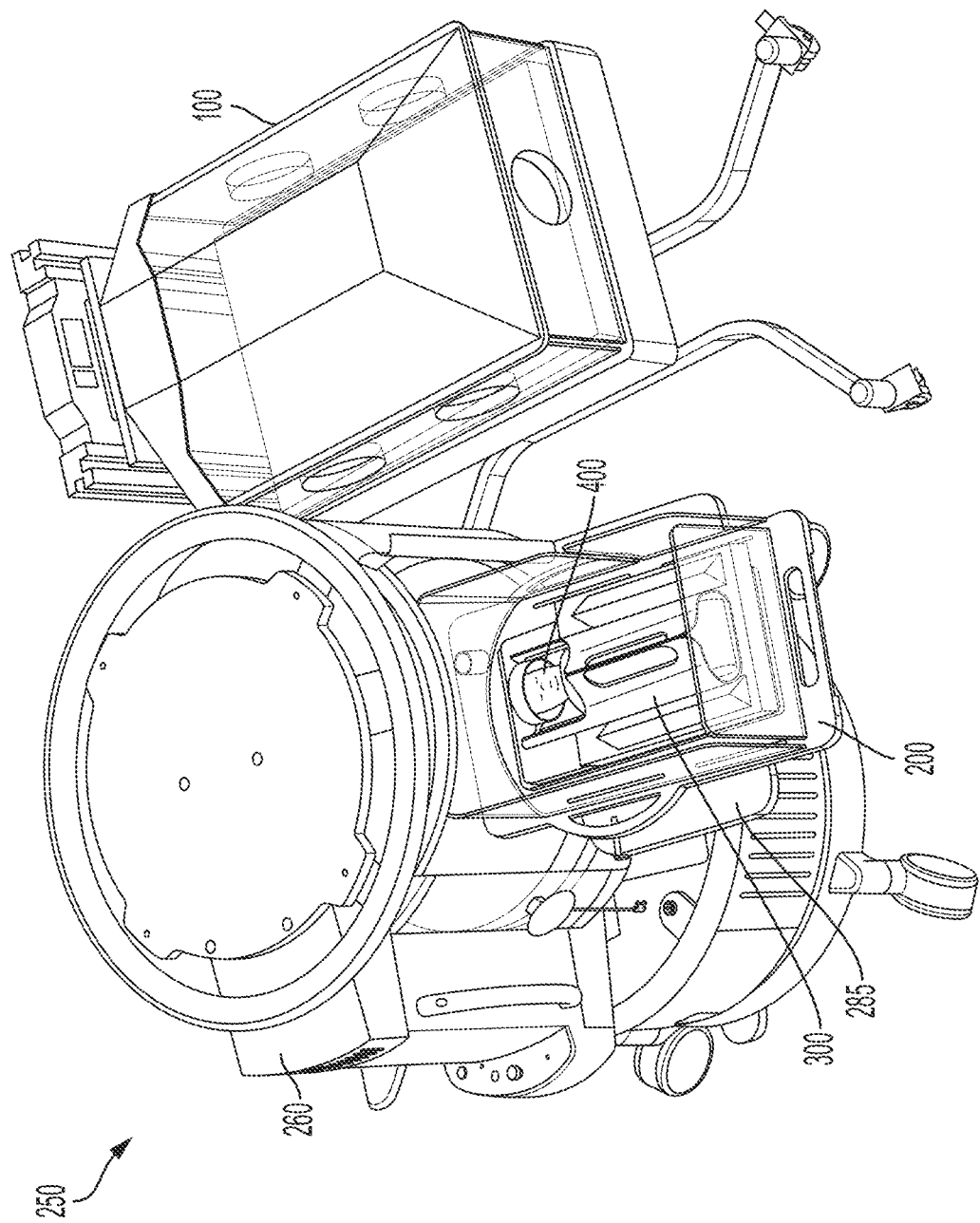
FIG. 10 illustrates the example MR isolette system of FIG. 9 having an infant positioned within and being coupled to an MRI device, in accordance with some embodiments of the technology described herein.

FIG. 10 illustrates the example MR isolette system of FIG. 9 having an infant positioned therein and being coupled to an MRI device, in accordance with some embodiments of the technology described herein. As shown in FIG. 10, the infant 400 and infant-carrying apparatus 300 may be moved from the conventional isolette 100 to the MR isolette 200. The MR isolette 200 may be initially positioned at least partially outside of an imaging region of the MRI device 260 such that the MR isolette is easily accessible for positioning the infant 400 and infant-carrying apparatus 300 therein. For example, in the illustrated embodiment, the MR isolette 200 is supported by bridge 285 removably coupled to the MRI device 260. As described herein, bridge 285 may be removably coupled to MRI device 260 at different locations around the perimeter of the MRI device 260 to facilitate insertion of the MR isolette 200 at any desired location.

Figure 11A:
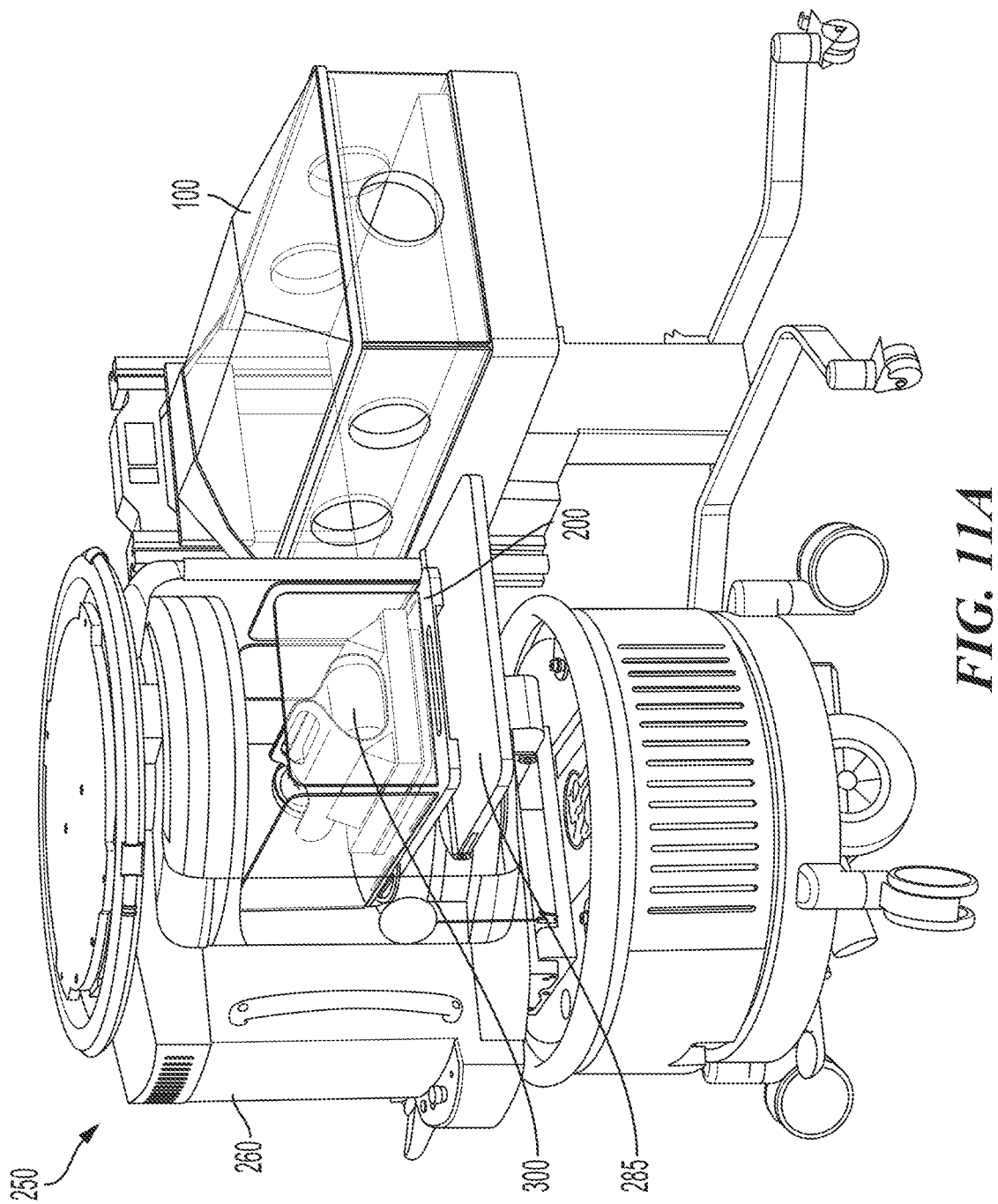
FIGS. 11A-11B illustrate the example MR isolette system of FIG. 9, having at least a part of the infant positioned within an imaging region of an MRI device, in accordance with some embodiments of the technology described herein.
Figure 11B:
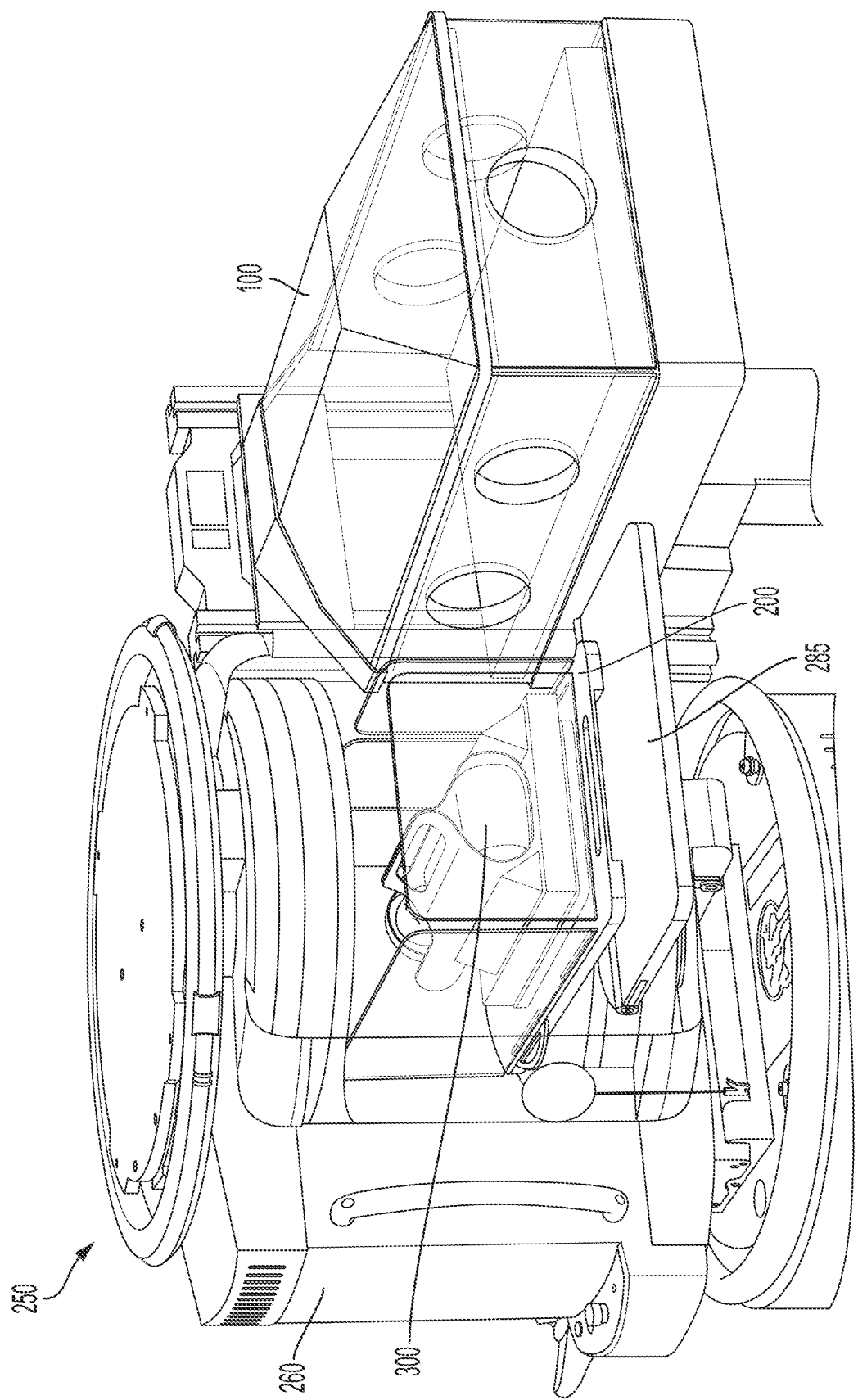

FIGS. 11A-11B illustrate the example MR isolette system of FIG. 9, having at least a part of the infant positioned within an imaging region of the MRI device, in accordance with some embodiments of the technology described herein. As shown in FIGS. 11A-11B, the MR isolette 200 may be pushed at least partially into an imaging region of the MRI device 260 such that at least a part of the infant 400 is disposed within the imaging region for MR imaging. As described herein, various components of the MR isolette system 250 may facilitate centering the desired portion of the infant 400 within an isocenter of the imaging region (e.g., infant-carrying apparatus 300, receptacle 275, padding 410, raised portions 420, etc.). For example, the MR isolette 200 may be slid into the imaging region until the complementary portion of the MRI device 260 is received in the receptacle 275 of MR isolette 200. When positioned, receptacle 275 and tracks 277 may prevent the isolette 200 from being moved further into the imaging region in vertical, longitudinal, and lateral directions, such that once the MR isolette 200 is positioned, the only direction the MR isolette 200 can be moved in is backwards out of the imaging region. Once the desired portion of the infant 400 is positioned within the imaging region, one or more MR images of at least the portion of the infant 400 may be obtained.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present disclosure need not reside on a single computer or processor, but may be distributed in a modular fashion among a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

The above-described embodiments of the present technology can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as a controller that controls the above-described function. A controller can be implemented in numerous ways, such as with dedicated hardware, or with general purpose hardware (e.g., one or more processor) that is programmed using microcode or software to perform the functions recited above, and may be implemented in a combination of ways when the controller corresponds to multiple components of a system.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The terms "substantially", "approximately", and "about" may be used to mean within ±20% of a target value in some embodiments, within ±10% of a target value in some embodiments, within ±5% of a target value in some embodiments, within ±2% of a target value in some embodiments. The terms "approximately" and "about" may include the target value.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. An infant-carrying apparatus to facilitate imaging an infant using a magnetic resonance imaging (MRI) device, the apparatus comprising:
    an infant support to support the infant during imaging, the infant support comprising:
        a jacket; and
        padding coupled to the jacket, wherein the padding comprises an inner swaddle disposed on an interior of the jacket; and at least one radio frequency (RF) coil integrated with the infant support, the at least one RF coil configured to detect MR signals during MR imaging.

2. The infant-carrying apparatus of claim 1, wherein the at least one RF coil comprises an RF head coil coupled to the infant support at a position for at least partially encircling the infant's head.

3. The infant-carrying apparatus of claim 1, wherein the at least one RF coil comprises an RF body coil coupled to the infant support at a first position for at least partially encircling the infant's body, and a RF head coil coupled to the infant support at a second position for at least partially encircling the infant's head.

4. The infant-carrying apparatus of claim 3, wherein the RF body coil is configured to transmit RF pulses according to one or more pulse sequences during imaging performed by the MRI device.

5. The infant-carrying apparatus of claim 1, wherein the at least one RF coil is configured to form a loop when the infant-carrying apparatus is in an open configuration.

6. The infant-carrying apparatus of claim 1, wherein the at least one RF coil comprises a flexible loop.

7. The infant-carrying apparatus of claim 1, further comprising head pads removably coupled to the infant-carrying apparatus.

8. The infant-carrying apparatus of claim 7, wherein the head pads provide acoustic dampening to mitigate acoustic noise generated by MR pulse sequences during image acquisition.

9. The infant-carrying apparatus of claim 1, wherein the jacket comprises a left side and a right side, and the left side of the jacket is configured to be coupled to the right side of the jacket via at least one fastener.

10. An infant-carrying apparatus to facilitate imaging an infant using a magnetic resonance imaging (MRI) device, the apparatus comprising:
    an infant support to support the infant during imaging, the infant support comprising:
    a jacket; and
    padding detachably coupled to the jacket; and
    at least one radio frequency (RF) coil integrated with the infant support, the at least one RF coil configured to detect MR signals during MR imaging.

11. The infant-carrying apparatus of claim 10, wherein the at least one RF coil comprises an RF head coil coupled to the infant support at a position for at least partially encircling the infant's head.

12. The infant-carrying apparatus of claim 10, wherein the at least one RF coil comprises an RF body coil coupled to the infant support at a first position for at least partially encircling the infant's body, and a RF head coil coupled to the infant support at a second position for at least partially encircling the infant's head.

13. The infant-carrying apparatus of claim 12, wherein the RF body coil is configured to transmit RF pulses according to one or more pulse sequences during imaging performed by the MRI device.

14. The infant-carrying apparatus of claim 10, wherein the at least one RF coil is configured to form a loop when the infant-carrying apparatus is in an open configuration.

15. An infant-carrying apparatus to facilitate imaging an infant using a magnetic resonance imaging (MRI) device, the apparatus comprising:
    an infant support to support the infant during imaging, the infant support comprising:
    a jacket, wherein the jacket comprises handholds; and
    padding coupled to the jacket; and
    at least one radio frequency (RF) coil integrated with the infant support, the at least one RF coil configured to detect MR signals during MR imaging.

16. The infant-carrying apparatus of claim 15, wherein the at least one RF coil comprises an RF head coil coupled to the infant support at a position for at least partially encircling the infant's head.

17. The infant-carrying apparatus of claim 15, wherein the at least one RF coil comprises an RF body coil coupled to the infant support at a first position for at least partially encircling the infant's body, and a RF head coil coupled to the infant support at a second position for at least partially encircling the infant's head.

18. The infant-carrying apparatus of claim 17, wherein the RF body coil is configured to transmit RF pulses according to one or more pulse sequences during imaging performed by the MRI device.

19. The infant-carrying apparatus of claim 15, wherein the at least one RF coil is configured to form a loop when the infant-carrying apparatus is in an open configuration.

20. The infant-carrying apparatus of claim 15, wherein the at least one RF coil comprises a flexible loop.

\* \* \* \* \*